(12) United States Patent
Yano et al.

(10) Patent No.: US 10,508,124 B2
(45) Date of Patent: Dec. 17, 2019

(54) XANTHENE PROTECTIVE AGENT

(71) Applicant: SEKISUI MEDICAL CO., LTD., Chuo-ku (JP)

(72) Inventors: Shinya Yano, Chuo-ku (JP); Toshihiro Mori, Chuo-ku (JP); Hideki Kubota, Chuo-ku (JP)

(73) Assignee: SEKISUI MEDICAL CO., LTD., Chuo-ku (JP)

( * ) Notice: Subject to any disclaimer, the term of this patent is extended or adjusted under 35 U.S.C. 154(b) by 0 days.

(21) Appl. No.: 16/319,581

(22) PCT Filed: Jul. 24, 2017

(86) PCT No.: PCT/JP2017/026670
§ 371 (c)(1),
(2) Date: Jan. 22, 2019

(87) PCT Pub. No.: WO2018/021233
PCT Pub. Date: Feb. 1, 2018

(65) Prior Publication Data
US 2019/0263842 A1 Aug. 29, 2019

(30) Foreign Application Priority Data

Jul. 25, 2016 (JP) ................... 2016-145022
Feb. 15, 2017 (JP) ................... 2017-025508

(51) Int. Cl.
C07F 7/18 (2006.01)
C07K 1/06 (2006.01)
C07B 51/00 (2006.01)

(52) U.S. Cl.
CPC ............ C07F 7/1804 (2013.01); C07K 1/062 (2013.01); C07K 1/063 (2013.01); C07K 1/064 (2013.01); C07K 1/065 (2013.01); C07K 1/066 (2013.01); C07K 1/067 (2013.01); C07B 51/00 (2013.01)

(58) Field of Classification Search
CPC .................................... C07F 7/1804
USPC ........................................ 549/391
See application file for complete search history.

(56) References Cited

U.S. PATENT DOCUMENTS

2010/0249374 A1 9/2010 Takahashi
2012/0059149 A1 3/2012 Takahashi

FOREIGN PATENT DOCUMENTS

WO WO 2010/113939 A1 10/2010
WO WO 2012/029794 A1 3/2012
WO WO 2017/038650 A1 3/2017

OTHER PUBLICATIONS

International Search Report dated Sep. 19, 2017, in PCT/JP2017/026670 filed on Jul. 24, 2017.

Li, J. et al. ""Singapore Green": A New Fluorescent Dye for Microarray and Bioimaging Applications", Organic Letters, 2009, vol. 11, No. 2, pp. 405-408, total 4 pages.
Casillas, L. K. et al., "Total Synthesis of O-Methylsterigmatocystin Using N-Alkylnitrilium Salts and Carbonyl-Alkene Interconversion in a New Xanthone Synthesis", Journal of Organic Chemistry, 1999, vol. 64, No. 11, pp. 4050-4059.
Fonteneau, N. et al., "Synthesis of quinone and xanthone analogs of rhein", Tetrahedron, 2001, vol. 57, No. 44, pp. 9131-9135.

Primary Examiner — Taofiq A Solola
(74) Attorney, Agent, or Firm — Oblon, McClelland, Maier & Neustadt, L.L.P.

(57) ABSTRACT

To develop a protecting group that facilitates separation and purification, after reaction, of a compound including a protected functional group, without solidifying or insolubilizing the compound.
A xanthene compound of by General Formula (1)

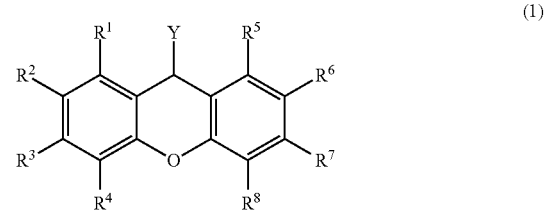

(1)

(wherein Y is $-OR^{17}$ ($R^{17}$ is a hydrogen atom or an active ester-protecting group), $-NHR^{18}$ ($R^{18}$ is a hydrogen atom, or a linear or branched $C_1$-$C_6$ alkyl group or aralkyl group), an azide, a halogen atom, or a carbonyl group formed together with a methylene group;
at least one of $R^1$ to $R^8$ is represented by Formula (2);

$$-O-R^9-X-A \quad (2)$$

and a residue is a hydrogen atom, a halogen atom, a $C_1$-$C_4$ alkyl group, or a $C_1$-$C_4$ alkoxy group,
wherein $R^9$ is a linear or branched $C_1$-$C_{16}$ alkylene group;
X is O or $CONR^{19}$ ($R^{19}$ is a hydrogen atom or a $C_1$-$C_4$ alkyl group); and
A is represented by Formula (3) or the like

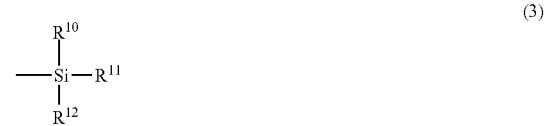

(3)

(wherein $R^{10}$, $R^{11}$, and $R^{12}$, the same or different, are a linear or branched $C_1$-$C_6$ alkyl group or an aryl group optionally including a substituent;
$R^{13}$ is a single bond or a linear or branched $C_1$-$C_3$ alkylene group; and
$R^{14}$, $R^{15}$, and $R^{16}$ are a linear or branched $C_1$-$C_3$ alkylene group)).

12 Claims, 1 Drawing Sheet

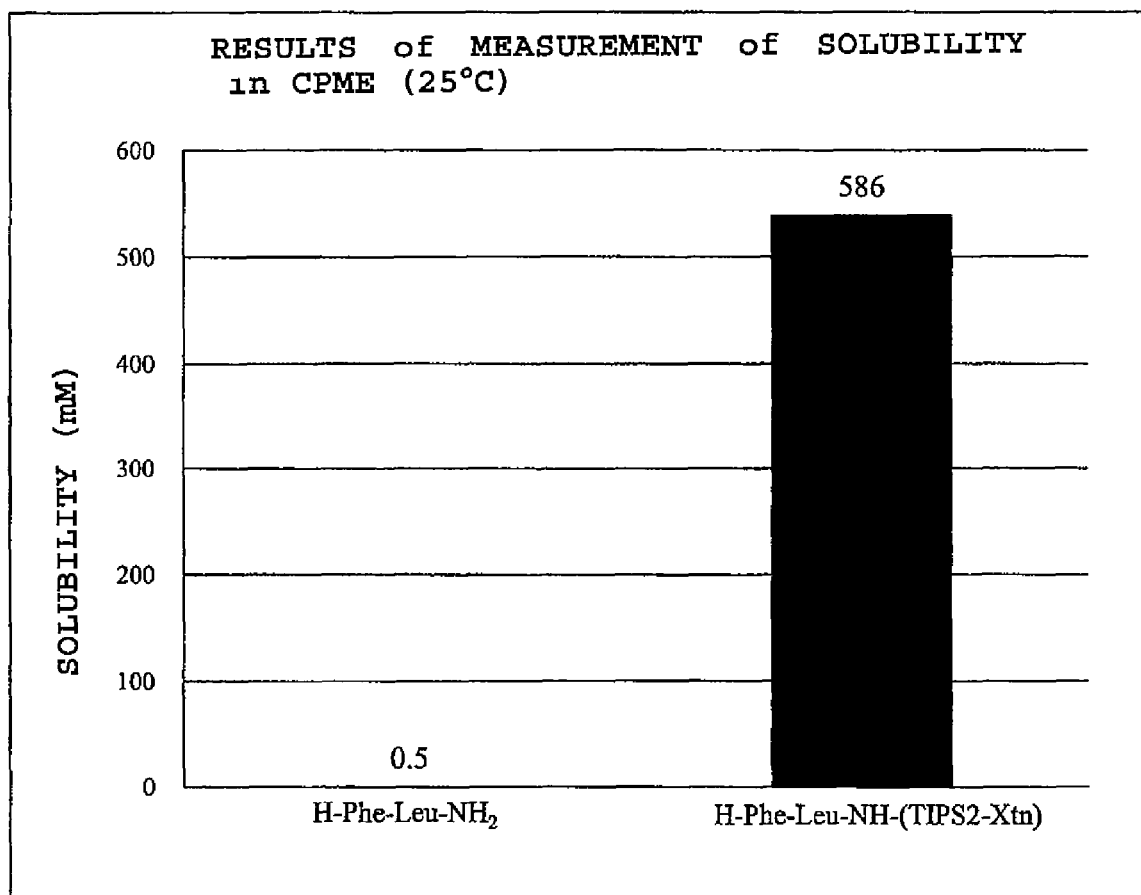

XANTHENE PROTECTIVE AGENT

FIELD OF THE INVENTION

The present invention relates to a new xanthene compound useful as a protective agent for protecting, for example, a carboxy group, a hydroxy group, a diol group, an amino group, an amide group, or a mercapto group.

BACKGROUND OF THE INVENTION

In peptide synthesis or synthesis of various compounds, some reactions require protection of functional groups such as a carboxy group, a hydroxy group, a diol group, an amino group, an amide group, and a mercapto group. A protecting group for those functional groups is required to be capable of protecting the functional groups by a simple method and being removed from the functional groups under moderate conditions. Benzyl ester (Bn), and tert-butyl ester are known as examples of a protecting group for a carboxy group. According to recent reports (Patent Literatures 1 and 2), benzyl alcohol compounds and diphenylmethane compounds are found to be useful as protecting groups.

CITATION LIST

Patent Literature

Patent Literature 1: WO 2012/029794 A
Patent Literature 2: WO 2010/113939 A

SUMMARY OF THE INVENTION

Technical Problem

However, deposition is a disadvantage commonly found in a compound that includes a functional group protected by a protecting group in the related art. Particularly, in peptide synthesis, such a compound is insoluble in an organic solvent, which often causes difficulty in separation and purification of the compound after reaction. The difficulty in separation and purification is a major problem in peptide synthesis where a condensation reaction is carried out continuously.

Accordingly, an object of the present invention is to improve solubility, in an organic solvent, of a compound including a protected functional group, whereby offering a protecting group that facilitates separation and purification of the compound after reaction, without solidifying or insolubilizing the compound.

Solution to the Problem

As a result of extensive studies on substituents of xanthene compounds, the present inventors have developed a compound having a trialkylsilyloxy substitutent at the terminal of an oxyalkylene group by which the substituent is connected to a benzene ring of a xanthene compound. The present inventors have found that a compound including a functional group protected by the xanthene compound hardly deposits in an organic solvent and is easily separated and purified by liquid-liquid phase separation, and that the compound is useful as a protective agent, whereby completing the invention.

In other words, the present invention is to provide the following [1] to [12].

[1] A xanthene compound of General Formula (1)

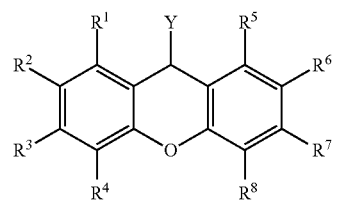

(1)

(wherein Y is —OR$^{17}$ (R$^{17}$ is a hydrogen atom or an active ester-protecting group), —NHR$^{18}$ (R$^{18}$ is a hydrogen atom, or a linear or branched C$_1$-C$_6$ alkyl group or aralkyl group), an azide, a halogen atom, or a carbonyl group formed together with a methylene group;

at least one of R$^1$ to R$^8$ is represented by Formula (2);

and a residue is a hydrogen atom, a halogen atom, a C$_1$-C$_4$ alkyl group, or a C$_1$-C$_4$ alkoxy group, wherein R$^9$ is a linear or branched C$_1$-C$_{16}$ alkylene group;

X is O or CONR$^{19}$ (R$^{19}$ is a hydrogen atom or a C$_1$-C$_4$ alkyl group); and A is represented by Formula (3), (4), (5), (6), (7), (8), (9), (10), (11), (12), or (13)

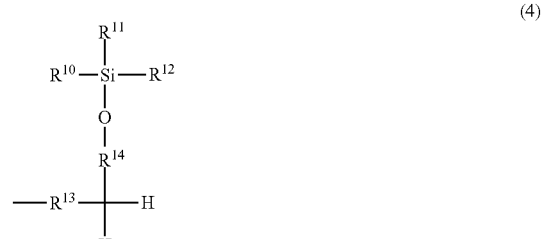

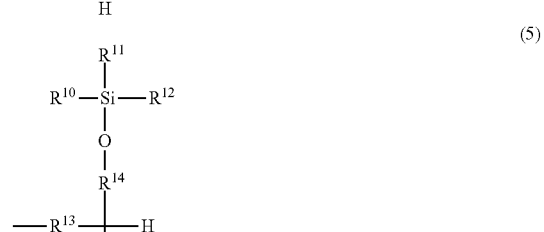

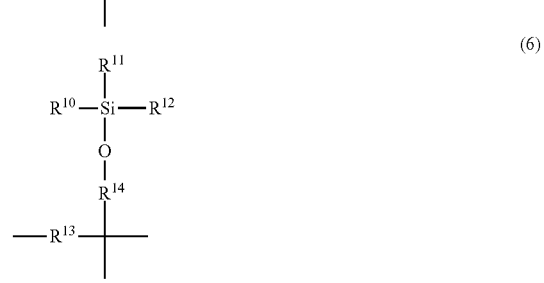

-continued (7)
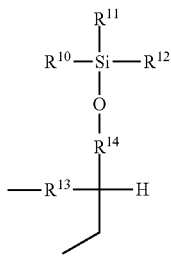

(8)
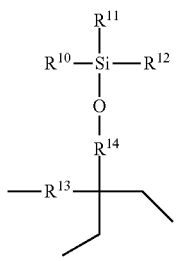

(9)
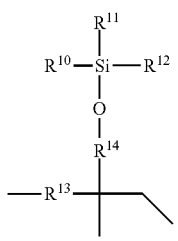

(10)
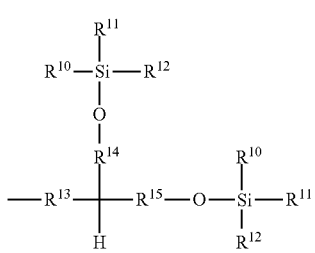

(11)
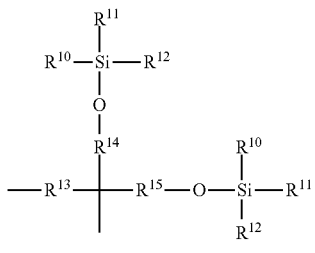

(12)
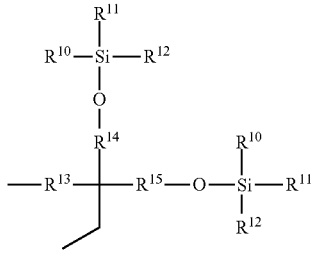

(13)
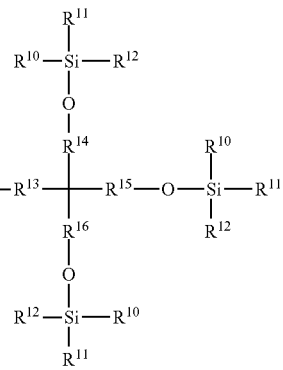

(wherein $R^{10}$, $R^{11}$, and $R^{12}$, the same or different, are a linear or branched $C_1$-$C_6$ alkyl group or an aryl group optionally including a substituent;

$R^{13}$ is a single bond or a linear or branched $C_1$-$C_3$ alkylene group; and $R^{14}$, $R^{15}$, and $R^{16}$ are a linear or branched $C_1$-$C_3$ alkylene group)).

[2] The xanthene compound according to [1], wherein Y is —$OR^7$ ($R^{17}$ is a hydrogen atom or an active ester-protecting group), —$NHR^{18}$ ($R^{18}$ is a hydrogen atom, or a linear or branched $C_1$-$C_6$ alkyl group or aralkyl group), an azide, or a halogen atom.

[3] The xanthene compound according to [1], wherein Y is —$OR^{17}$ ($R^{17}$ is a hydrogen atom or an active ester-protecting group), or —$NHR^8$ ($R^{18}$ is a hydrogen atom, or a linear or branched $C_1$-$C_6$ alkyl group or aralkyl group).

[4] The xanthene compound according to [1], wherein Y is —$OR^7$ ($R^{17}$ is a hydrogen atom), —$NHR^{18}$ ($R^{18}$ is a hydrogen atom), or a carbonyl group formed together with a methylene group.

[5] The xanthene compound according to [1], wherein Y is —$OR^7$ ($R^{17}$ is a hydrogen atom), or —$NHR^{18}$ ($R^{18}$ is a hydrogen atom).

[6] The xanthene compound according to any one of [1] to [5], wherein at least one of $R^1$ to $R^8$ is a group represented by Formula (2), and a residue is a hydrogen atom, a $C_1$-$C_4$ alkyl group, or a $C_1$-$C_4$ alkoxy group.

[7] The xanthene compound according to any one of [1] to [6], wherein $R^9$ is a linear or branched $C_2$-$C_{16}$ alkylene group.

[8] The xanthene compound according to any one of [1] to [7], wherein $R^9$ is a linear or branched $C_5$-$C_{16}$ alkylene group.

[9] The xanthene compound according to any one of [1] to [8], wherein $R^{13}$ is a single bond or a methylene group, and $R^{14}$, $R^{15}$, and $R^{16}$ are a methylene group.

[10] A protective agent for protecting a carboxy group, a hydroxy group, a diol group, an amino group, an amide group, or a mercapto group, wherein the protective agent contains the xanthene compound according to any one of [1] to [9].

[11] A method for producing a compound with a protective agent for protecting a carboxy group, a hydroxy group, a diol group, an amino group, an amide group, or a mercapto group, wherein the protective agent contains the xanthene compound according to any one of [1] to [9].

[12] A method for producing a peptide with a protective agent for protecting a carboxy group, a hydroxy group, a diol group, an amino group, an amide group, or a mercapto group, wherein the protective agent contains the xanthene compound according to any one of [11] to [9].

Effects of the Invention

A compound that includes a functional group protected by the xanthene compound (1) of the present invention liquefies easily and has enhanced solubility in a solvent. Therefore, the compound after a condensation reaction is easily separated and purified by liquid-liquid phase separation.

When insolubilization and fixation of raw materials or intermediates are obstacles to production of various chemical substances such as medicine and agricultural chemicals, binding the xanthene compound (1) of the present invention to the raw materials or intermediate compounds improves solubility of the raw materials or intermediate compounds, which leads to solution to the above problems.

BRIEF DESCRIPTION OF THE DRAWINGS

FIG. 1 shows measurement results on solubility in cyclopentyl methyl ether (CPME).

DESCRIPTION OF THE EMBODIMENTS

In a xanthene compound of General Formula (1) according to the present invention, at least one of $R^1$ to $R^8$ has a structure represented by Formula (2). With such a structure, a compound protected by this xanthene compound (1) liquefies easily and has markedly enhanced solubility in a solvent.

In General Formula (1), Y is —$OR^7$ ($R^{17}$ is a hydrogen atom or an active ester-protecting group), —$NHR^{18}$ ($R^{18}$ is a hydrogen atom, or a linear or branched $C_1$-$C_6$ alkyl group or aralkyl group), an azide, a halogen atom, or a carbonyl group formed together with a methylene group. Examples of the halogen atom include a fluorine atom, a bromine atom, a chlorine atom, and an iodine atom.

Examples of the active ester-protecting group include an active ester-carbonyl group, and an active ester-sulfonyl group. Examples of the active ester-carbonyl group include carbonyloxysuccinimide, an alkoxycarbonyl group, an aryloxycarbonyl group, and an aralkyloxycarbonyl group, and a preferable example is carbonyloxysuccinimide.

Examples of the active ester-sulfonyl group include an alkylsulfonyl group and an arylsulfonyl group, and preferable examples are a $C_1$-$C_6$ alkylsulfonyl group and a p-toluenesulfonyl group.

Y is preferably —$OR^{17}$ ($R^{17}$ is a hydrogen atom or an active ester-protecting group), —$NHR^{18}$ ($R^{18}$ is a hydrogen atom, or a linear or branched $C_1$-$C_6$ alkyl group or aralkyl group), an azide, or a halogen atom.

More preferably, Y is —$OR^{17}$ ($R^{17}$ is a hydrogen atom or an active ester-protecting group), or —$NHR^{18}$ ($R^{18}$ is a hydrogen atom, or a linear or branched $C_1$-$C_6$ alkyl group or aralkyl group).

Still more preferably, Y is —$OR^{17}$ ($R^{17}$ is a hydrogen atom), or —$NHR^{18}$ ($R^{18}$ is a hydrogen atom).

In the xanthene compound of the present invention, at least one of $R^1$ to $R^8$ is a group represented by Formula (2), and it is preferable that one or two of them are groups represented by Formula (2).

A residue is a hydrogen atom, a halogen atom, a $C_1$-$C_4$ alkyl group, or a $C_1$-$C_4$ alkoxy group. Examples of the residual halogen atom represented by $R^1$ to $R^8$ include a fluorine atom, a chlorine atom, and a bromine atom. Among these examples, a fluorine atom and a chlorine atom are preferable. Examples of the residual $C_1$-$C_4$ alkoxy group include methoxy groups, ethoxy groups, n-propyloxy groups, isopropyloxy groups, and n-butyloxy groups. Among these examples, methoxy groups are preferable. Examples of the $C_1$-$C_4$ alkyl group include methyl groups, ethyl groups, n-propyl groups, isopropyl groups, and n-butyl groups. Among these examples, methyl groups are preferable.

$R^9$ is a linear or branched $C_1$-$C_{16}$ alkylene group. From a viewpoint of improving the solubility, in a solvent, of the compound to which the xanthene compound (1) is bound, the number of carbon atoms of the alkylene group is preferably 2 or more, more preferably, 6 or more, still more preferably, 8 or more, and preferably, 16 or less, more preferably, 14 or less, still more preferably 12 or less.

The alkylene group is preferably a linear or branched $C_2$-$C_{16}$ alkylene group, more preferably, a linear or branched $C_6$-$C_{16}$ alkylene group, still more preferably, a linear or branched $C_8$-$C_{14}$ alkylene group, and still more preferably, a linear or branched $C_8$-$C_{12}$ alkylene group. Specific examples of the alkylene group include methylene groups, ethylene groups, trimethylene groups, tetramethylene groups, pentamethylene groups, hexamethylene groups, heptamethylene groups, octamethylene groups, nanomethylene groups, decamethylene groups, undecamethylene groups, dodeca methylene groups, and tetradecamethylene groups.

X is O or $CONR^9$.

Herein, $R^{19}$ is a hydrogen atom or a $C_1$-$C_4$ alkyl group and is preferably a hydrogen atom.

A is a group represented by Formula (3), (4), (5), (6), (7), (8), (9), (10), (11), (12), or (13). $R^{10}$, $R^{11}$, and $R^{12}$, the same or different, are a linear or branched $C_1$-$C_6$ alkyl group or an aryl group optionally including a substituent. Examples of the $C_1$-$C_6$ alkyl group include methyl groups, ethyl groups, n-propyl groups, isopropyl groups, n-butyl groups, isobutyl groups, sec-butyl groups, tert-butyl groups, n-pentyl groups, and n-hexyl groups. Among these examples, a $C_1$-$C_4$ alkyl group is preferable, and methyl groups, tert-butyl groups, and isopropyl groups are more preferable.

Examples of the aryl group which may have a substituent include a $C_6$-$C_{10}$ aryl group, and specific examples thereof include a phenyl group and a naphthyl group in which a $C_1$-$C_3$ alkyl group may be substituted by another group. Among these examples, a phenyl group is more preferable.

$R^{13}$ is a single bond or a linear or branched $C_1$-$C_3$ alkylene group. Examples of the linear or branched $C_1$-$C_3$ alkylene group include methylene groups, ethylene groups, trimethylene groups, and propylene groups. Among these examples, a single bond is particularly preferable.

$R^{14}$, $R^{15}$, and $R^{16}$ are a linear or branched $C_1$-$C_3$ alkylene group. Examples of the linear or branched $C_1$-$C_3$ alkylene group include methylene groups, ethylene groups, trimethylene groups, and propylene groups, and methylene groups are particularly preferable.

More preferably, the compound is such that, in General Formula (1), Y is —$OR^{17}$ ($R^{17}$ is a hydrogen atom), or —$NHR^{18}$ ($R^{18}$ is a hydrogen atom); at least one of $R^1$ to $R^5$, preferably one or two of $R^1$ to $R^8$ are represented by Formula (2), and a residue is a hydrogen atom, a $C_1$-$C_4$ alkyl group, or a $C_1$-$C_4$ alkoxy group; $R^9$ is a linear or branched $C_2$-$C_{16}$ alkylene group; $R^{13}$ is a single bond or a methylene group; and $R^{14}$, $R^{15}$, and $R^{16}$ are a methylene group.

Still more preferably, the compound is such that, in Formula (2), $R^9$ is a linear or branched $C_6$-$C_{16}$ alkyl group; X is O or CONH; A is a group represented by Formula (3)

or (13); $R^{10}$, $R^{11}$, and $R^{12}$, the same or different, are a $C_1$-$C_4$ alkyl group; $R^{13}$ is a single bond; and $R^{14}$, $R^{15}$, and $R^{16}$ are a methylene group.

The following structure is preferable as a structure in which Y and $R^1$ to $R^8$ in Formula (1) are substituted by other groups.

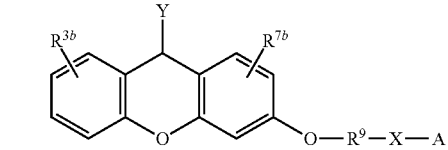
(1-1)

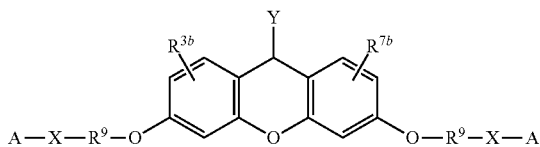
(1-2)

(wherein $R^{3b}$ and $R^{7b}$ are hydrogen atoms, a $C_1$-$C_4$ alkyl group, or a $C_1$-$C_4$ alkoxy group; and Y, A, X and $R^9$ are the same as above.)

Examples of the xanthene compound (1) of the present invention include the following (a) to (e).

(a) TIPS2-PP Protective Agent

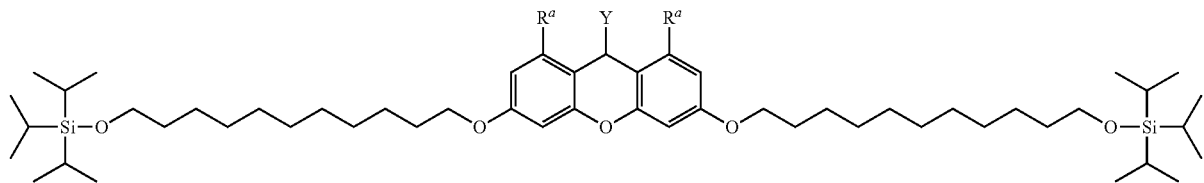

(wherein Y is —$OR^{17}$ ($R^{17}$ is a hydrogen atom), or —$NHR^{18}$ ($R^{18}$ is a hydrogen atom), $R^a$ is a hydrogen atom, a $C_1$-$C_4$ alkyl group, or a $C_1$-$C_4$ alkoxy group.)

(b) TIPS3-P Protective Agent

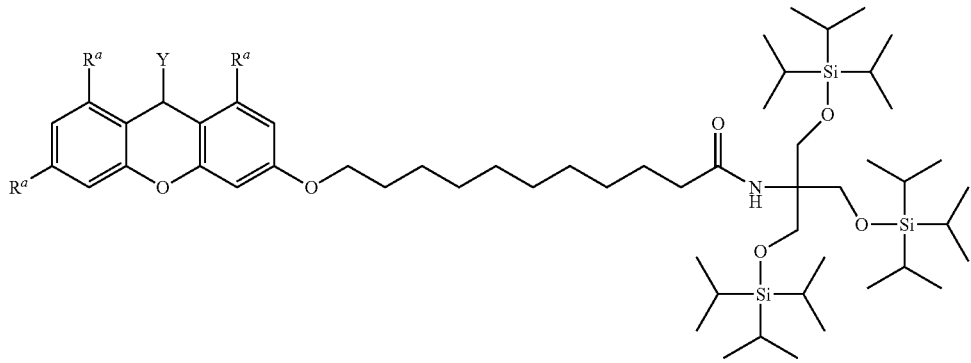

(wherein Y and $R^a$ are the same as in (a).)

(c) TIPS4-PP Protective Agent

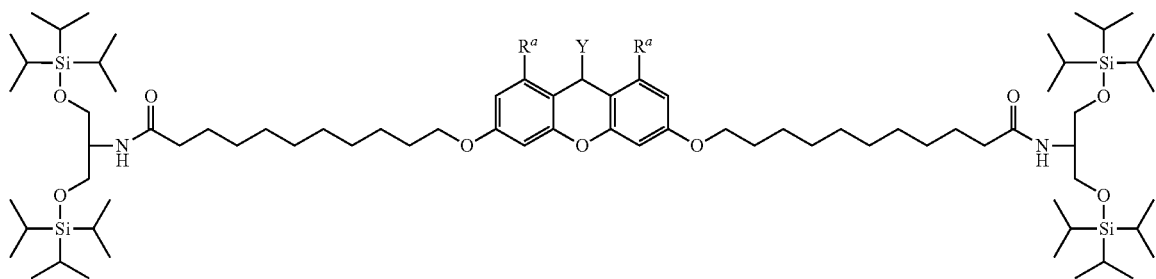

(wherein Y and $R^a$ are the same as in (a).)

(d) TIPS6-PP Protective Agent

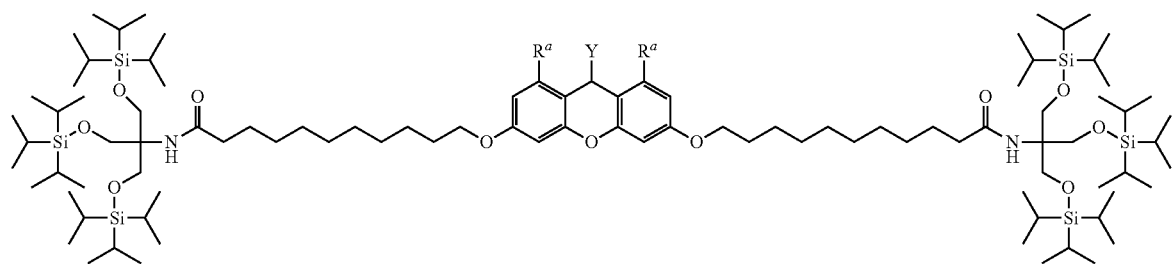

(wherein Y and $R^a$ are the same as in (a).)

(e) TBDPS2-PP Protective Agent

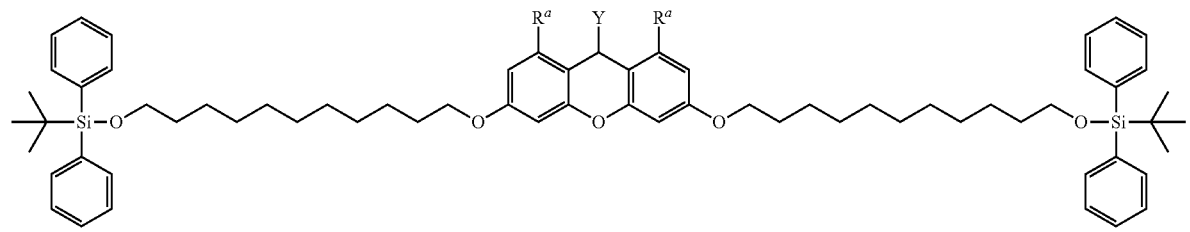

(wherein Y and $R^a$ are the same as in (a).)

The xanthene compound (1) of the present invention is produced, for example, according to the following reaction formula.

(wherein Hal is a halogen atom; at least one of $R^{1a}$ to $R^{8a}$ is a hydroxy group, and a residue is a hydrogen atom, a halogen atom, a $C_1$-$C_4$ alkyl group, or a $C_1$-$C_4$ alkoxy group; B is an amino acid derivative including a mercapto group; Z is a compound including a —CONH— group; and $R^1$ to $R^8$, X, and A are the same as above.)

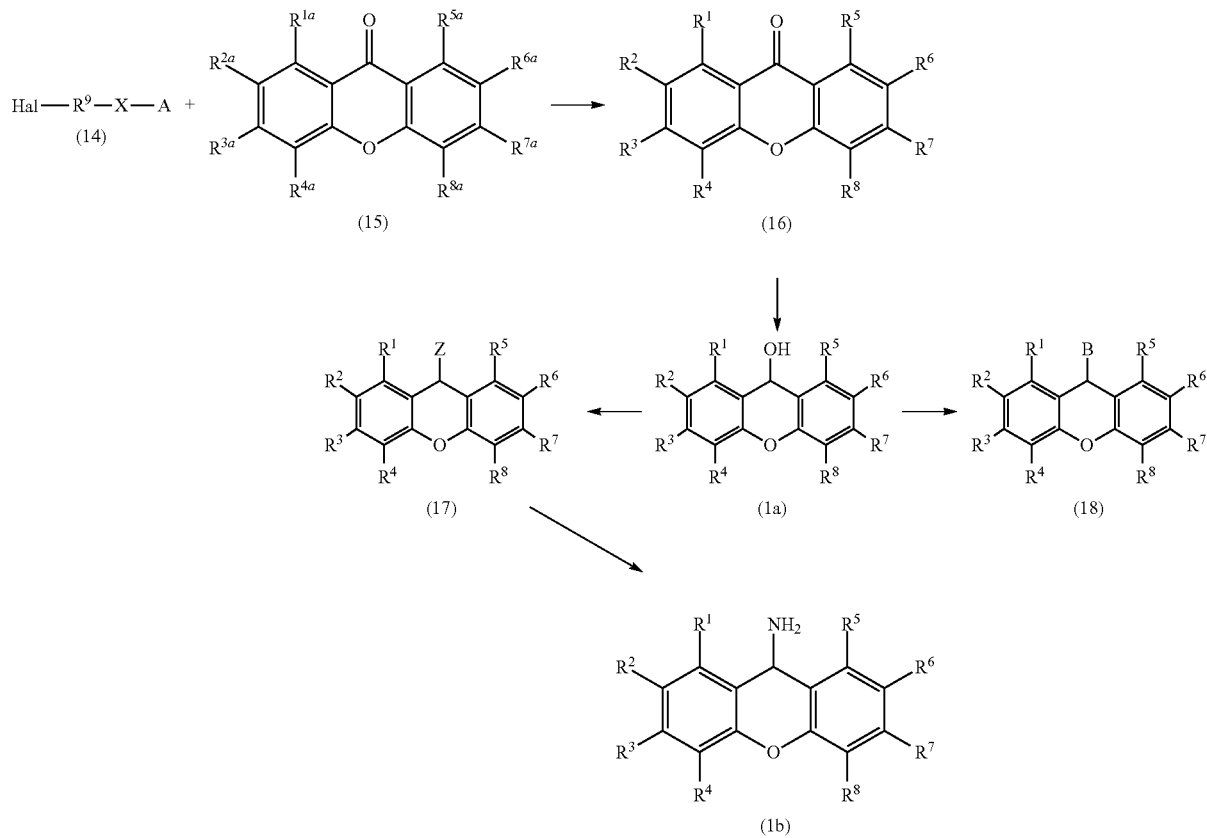

A silyloxylated alkyl halide (14) is reacted with a xanthene compound (15) to yield a silyloxylated xanthene compound (16). Next, a carbonyl group of the silyloxylated xanthene compound (16) is converted into a hydroxy group and reacted with a compound including a —$CONH_2$ group to yield a compound (17). Next, a protecting group of the compound (17) is deprotected to yield a compound (1b). Furthermore, a xanthene compound (1a) including a hydroxy group is reacted with an amino acid including a mercapto group or with an amino acid derivative including a mercapto group to yield a compound (18).

The silyloxylated alkyl halide (14) which is a raw material herein is produced, for example, by reacting a halogenated alcohol with a silylation agent in the presence of a base. An example of the halogen atom in the compound (14) includes a bromine atom.

Examples of the silylation agent used in the above reaction include triisopropylsilyl chloride (TIPSCl), triisopropylsilyl bromide, triisopropylsilyl iodide, methanesulfonyltriisopropylsilyl, trifluoromethanesulfonylisopropylsilyl, p-toluenesulfonyltriisopropylsilyl, tert-butyldiphenylchlorosilane (TBDPSCl), and tert-butyldimethylchlorosilane (TBSCl).

Examples of the base include organic bases such as TEA, DIPEA, DBU, diazabicyclononene (DBN), DABCO, imidazole, N-methylimidazole, N,N-dimethylaniline, pyridine, 2,6-lutidine, DMAP, LDA, NaOAc, MeONa, MeOK, lithium hexamethyldisilazide (LHMDS), and sodium bis(trimethylsilyl) amide (NaHMDS); and inorganic bases such as $Na_2CO_3$, $NaHCO_3$, NaH, $NaNH_2$, $K_2CO_3$, and $Cs_2CO_3$.

Examples of the solvent include hydrocarbons such as hexane and heptane; ethers such as diethyl ether, diisopropyl ether, cyclopentyl methyl ether (CPME), tetrahydrofuran, and dioxane; nitriles such as acetonitrile; amides such as dimethylformamide (DMF), dimethylacetamide, and hexamethylphosphoramide; sulfoxides such as dimethylsulfoxide; lactams such as N-methylpyrrolidone; hydrogen halides such as chloroform and dichloromethane; aromatic hydrocarbons such as toluene and xylene; and mixed solvents of these examples.

The reaction may be carried out, for example, at 0° C. to 100° C. for 1 hour to 24 hours.

The reaction of the silyloxylated alkyl halide (14) and the xanthene compound (15) is preferably carried out in the presence of a base.

Examples of the base used in the above reaction include organic bases such as TEA, DIPEA, DBU, DBN, DABCO, imidazole, N-methylimidazole, N,N-dimethylaniline, pyridine, 2,6-lutidine, DMAP, LDA, NaOAc, MeONa, MeOK, lithium hexamethyldisilazide (LHMDS), and sodium bis(trimethylsilyl) amide (NaHMDS); and inorganic bases such as $Na_2CO_3$, $NaHCO_3$, NaH, $K_2CO_3$, and $Cs_2CO_3$.

Examples of the solvent include hydrocarbons such as hexane and heptane; ethers such as diethyl ether, diisopropyl ether, CPME, tetrahydrofuran, and dioxane; nitriles such as acetonitrile; amides such as DMF, dimethylacetamide, and hexamethylphosphoramide; sulfoxides such as dimethylsulfoxide; lactams such as N-methylpyrrolidone; hydrogen halides such as chloroform and dichloromethane; aromatic hydrocarbons such as toluene and xylene; and mixed solvents of these examples.

The reaction may be carried out, for example, at 40° C. to 150° C. for 1 hour to 24 hours.

In regard to a method for converting a carbonyl group in the compound of Formula (16) into a hydroxy carbonyl group, an example of the method includes reduction with a reductant.

Examples of the reductant include lithium borohydride, sodium borohydride, lithium aluminum hydride, and aluminum hydride. Examples of the solvent include hydrocarbons such as hexane and heptane; alcohols such as methanol and ethanol; ethers such as diethyl ether, diisopropyl ether, CPME, tetrahydrofuran, and dioxane; aromatic hydrocarbons such as toluene and xylene; and mixed solvents of these examples. The reaction is preferably carried out, for example, at 0° C. to 90° C. for 1 hour to 120 hours.

In regard to the reaction between the compound of Formula (1a) and the compound including a —$CONH_2$ group, the compound of Formula (1a) is preferably reacted with the compound including a —$CONH_2$ group under an acid catalyst.

Examples of the compound including a —$CONH_2$ group include Fmoc-$NH_2$, ethyl carbamate, isopropyl carbamate, $AcNH_2$, $HCONH_2$, Cbz-$NH_2$, $CF_3CONH_2$, and Fmoc-amino acid-$NH_2$. Examples of the acid catalyst include acids such as trifluoromethanesulfonic acid, methanesulfonic acid, p-toluenesulfonic acid, acetic acid, hydrochloric acid, and sulfuric acid. Examples of the solvent include hydrocarbons such as hexane and heptane; ethers such as diethyl ether, diisopropyl ether, CPME, tetrahydrofuran, and dioxane; aromatic hydrocarbons such as toluene and xylene; hydrogen halides such as chloroform and dichloromethane; and mixed solvents of these examples. The reaction may be carried out, for example, at 20° C. to 150° C. for 0.5 hours to 48 hours.

To obtain the compound (1b) from the compound of Formula (17), it is preferable to treat the compound (17) with a base.

Examples of the base include bases such as diethylamine, piperidine, dimethylamine, DBU, morpholine, sodium hydroxide, and potassium hydroxide. Examples of the solvent include hydrocarbons such as hexane and heptane; ethers such as diethyl ether, diisopropyl ether, CPME, tetrahydrofuran, and dioxane; aromatic hydrocarbons such as toluene and xylene; hydrogen halides such as chloroform and dichloromethane; alcohols such as methanol, ethanol, and isopropyl alcohol; and mixed solvents of these examples. The reaction may be carried out, for example, at 0° C. to 150° C. for 0.5 hours to 48 hours.

In regard to the reaction between the compound of Formula (1a) and the amino acid derivative including a mercapto group, the compound of Formula (1a) is preferably reacted with an amino acid including a mercapto group or with the amino acid derivative including a mercapto group under an acid catalyst.

Examples of the amino acid including a mercapto group include Cysteine, homocysteine, mercaptonorvaline, and mercaptonorleucine. Examples of the amino acid derivative including a mercapto group include a compound in which an N-terminal of these examples of the amino acid is N-methylated; a compound in which an N-terminal of these examples of the amino acid is protected by, for example, a benzyloxycarbonyl (Cbz or Z) group, a fluorenylmethoxycarbonyl (Fmoc) group, an acetyl (Ac) group, a benzyl group, an allyl group, an allyloxycarbonyl (Aloc) group, a 2-nitrobenzenesulfonyl (Ns) group, a 2,4-dinitrobenzenesulfonyl (DNs) group, and a 4-nitrobenzenesulfonyl (Nos) group; a compound in which a C-terminal of these examples of the amino acid is protected by, for example, an amide group, a methyl ester group, an ethyl ester group, a tert-butyl ester group, a benzyl ester group, and an allyl ester group; a compound in which both N- and C-terminals are protected by a protecting group such as the examples above; and D-amino acid compounds corresponding to these examples.

Examples of the acid catalyst include acids such as trifluoromethanesulfonic acid, methanesulfonic acid, p-toluenesulfonic acid, acetic acid, hydrochloric acid, and sulfuric acid. Examples of the solvent include hydrocarbons such as hexane and heptane; ethers such as diethyl ether, diisopropyl ether, CPME, tetrahydrofuran, and dioxane; aromatic hydrocarbons such as toluene and xylene; hydrogen halides such as chloroform and dichloromethane; and mixed solvents of these examples. The reaction may be carried out, for example, at 20° C. to 150° C. for 0.5 hours to 24 hours.

The xanthene compound (1) of the present invention may be used as a protective agent for a functional group such as a carboxy group, a hydroxy group, a diol group, an amino group, an amide group, and a mercapto group. A compound in which a carboxy group, a hydroxy group, a diol group, an amino group, an amide group, or a mercapto group is protected by the xanthene compound (1) of the present invention is excellent in liquefaction property and solubility in a solvent. Therefore, the compound in which the functional group is protected by the xanthene compound (1) of the present invention as a protective agent is easily dissolved in an organic solvent and is easily separated and purified by, for example, liquid-liquid phase separation. In addition, the protecting group used in the compound of the present invention is easily removed by, for example, an acid or a catalytic reduction.

The compound protected by the xanthene compound (1) of the present invention may be a compound including a carboxy group, a hydroxy group, a diol group, an amino group, an amide group, or a mercapto group. Examples of such a compound include amino acids, peptides, saccharide compounds, proteins, nucleotides, various other pharmaceutical compounds and agrochemical compounds, and various other polymers and dendrimers.

An example of a method for synthesizing a peptide with the xanthene compound (1) of the present invention as a protective agent includes a method that involves the following steps (1) to (4). This method of peptide synthesis is particularly favorable in the industrial field since a protected peptide obtained in each step is separable by liquid-liquid phase separation.

If necessary, in an intermediate step, an intermediate compound may be temporarily isolated from a solution and purified, and then, undergo the next step, which makes the method more favorable in the industrial field.

(1) The xanthene compound (1) of the present invention is condensed with a C-terminal carboxy group of an N-protected amino acid or of an N-protected peptide in a soluble solvent so as to yield an N- and C-protected amino acid or an N- and C-protected peptide in which the C-terminal is protected by the xanthene compound (1) of the present invention. Alternatively, the xanthene compound (1) of the present invention is reacted with a C-terminal amide group of an N-protected amino acid or of an N-protected peptide in a soluble solvent so as to yield a N- and C-protected amino acid or an N- and C-protected peptide in which the C-terminal is protected by the xanthene compound (1) of the present invention.

(2) In regard to the N- and C-protected amino acid or the N- and C-protected peptide obtained herein, a protecting group is removed from the N terminal to yield a C-protected amino acid or a C-protected peptide.

(3) In regard to the C-protected amino acid or the C-protected peptide obtained herein, the N terminal is condensed with an N-protected amino acid or an N-protected peptide to yield an N- and C-protected peptide.

(4) In regard to the N- and C-protected peptide obtained herein, protecting groups are removed from the N terminal and from the C terminal to yield a desired peptide.

Examples of the soluble solvent include hydrocarbons such as hexane and heptane; ethers such as diethyl ether, diisopropyl ether, CPME, tetrahydrofuran, 2-methyltetrahydrofuran, 4-methyltetrahydropyran, dioxane, and methyl tert-butyl ether; esters such as ethyl acetate, butyl acetate, isopropyl acetate, and isobutyl acetate; hydrogen halides such as chloroform and dichloromethane; aromatic hydrocarbons such as toluene and xylene; and mixed solvents of these examples. These examples of the soluble solvent may be mixed with a solvent, for example, nitriles such as acetonitrile; amides such as DMF, dimethylacetamide, and hexamethylphosphoramide; sulfoxides such as dimethylsulfoxide; and lactams such as N-methylpyrrolidone.

Examples of a condensation reagent include COMU, HATU, HBTU, HCTU, TATU, TBTU, TCTU, TOTU, TDBTU, DEPBT, WSCI, WCSI/HCl, DCC, DIC, CDI, PyAop, PyBop, $T_3P$, and DMT-MM.

Examples of a condensation aid include Oxyma, HOAt, HOBt, HOOBt, HOCt, HOSu, HONb, and HOPht.

Examples of a base used in a condensation reaction include DIPEA, N-methylmorpholine, 2,4,6-trimethylpyridine, and DMAP.

The condensation reaction may be carried out, for example, at 0° C. to 40° C. for 10 minutes to 24 hours.

Examples of a remover for the N-terminal protecting group and the C-terminal protecting group include bases such as diethylamine, piperidine, dimethylamine, DBU, DABCO, triethylamine, morpholine, sodium carbonate, sodium tert-butoxide, potassium tert-butoxide; mixtures of these examples; acids such as acetic acid, formic acid, hydrochloric acid, sulfuric acid, trichloroacetic acid, trifluoroacetic acid, methanesulfonic acid, trifluoromethanesulfonic acid, p-toluenesulfonic acid, and hexafluoroisopropanol; and mixtures of these examples.

The N-terminal protecting group may be removed, for example, at 0° C. to 40° C. for 5 minutes to 24 hours.

The C-terminal protecting group may be removed, for example, at 0° C. to 40° C. for 30 minutes to 24 hours.

EXAMPLE

The present invention will hereinafter be described in detail with reference to Examples, but the present invention is not limited to Examples in any way.

Example 1

Synthesis of TIPS2-Xtn-OH

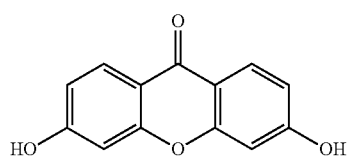

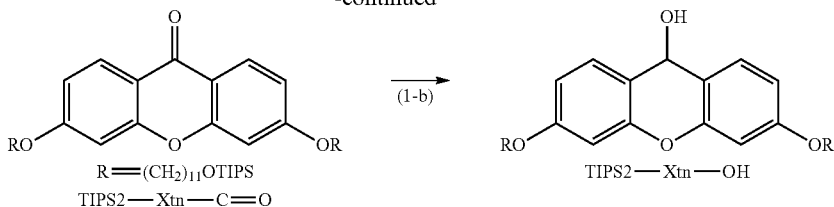

(Hereinafter, Br—(CH$_2$)$_{11}$—OTIPS, TIPS2-Xtn-C=O, and TIPS2-Xtn-OH represent the structures in the drawing.)

Example (1-a)

8.10 g (19.9 mmol) of Br—(CH$_2$)$_{11}$—OTIPS, 2.02 g (8.8 mmol) of 3,6-dihydroxyxanthone, and 4.39 g (31.8 mmol) of potassium carbonate were suspended in 58.9 mL of DMF, heated to 85° C., and stirred for 2 hours. The reaction solution was filtered, and the filtration residue was washed with 124 mL of heptane. The filtrate was separated to obtain a heptane layer. To the resulting heptane layer was added 59 mL of heptane, and the heptane layer was separated and washed with 59 mL of DMF. The heptane layer was separated and washed with the heptane and the DMF once more. To the resulting heptane layer, 59 mL of heptane was added, and the heptane layer was washed once with 59 mL of 1 N hydrochloric acid, once with 59 mL of a 5% sodium hydrogen carbonate aqueous solution, and twice with 59 mL of water. 59 mL was added to the resulting heptane layer, and the heptane layer was separated and washed once with 59 mL of DMF and twice with 59 mL of acetonitrile. The heptane layer was concentrated under reduced pressure, and a resulting residue was purified by silica gel column chromatography (heptane:ethyl acetate=70:1→0:100) to afford 7.85 g of TIPS2-Xtn-C=O.

$^1$H-NMR (400 MHz, CDCl$_3$) δ1.02-1.08 (m, 42H), 1.24-1.41 (m, 24H), 1.43-1.58 (m, 8H), 1.77-1.88 (m, 4H), 3.67 (t, 4H), 4.06 (t, 4H), 6.83 (d, 2H), 6.91 (dd, 2H), 8.2 2 (d, 2H)

$^{13}$C-NMR (100 MHz, CDCl$_3$) δ12.2 (6C), 18.2 (12C), 26.0 (2C), 26.1 (2C), 29.2-29.8 (12C), 33.2 (2C), 63.6 (2C), 68.8 (2C), 100.8 (2C), 113.4 (2C), 11 5.8 (2C), 128.2 (2C), 158.2 (2C), 164.4 (2C), 175.7

Example (1-b)

In a mixed solution of 2.3 mL of THF (anhydrous) and 0.45 mL of methanol, 0.30 g (0.34 mmol) of TIPS2-Xtn-C=O was dissolved, and 39 mg (1.02 mmol) of sodium borohydride was added to the mixed solution. The solution was heated to 55° C. and stirred for 1 hour and 40 minutes. To the solution, 39 mg (1.02 mmol) of sodium borohydride and 0.62 mL of methanol were added, and the solution was stirred at 55° C. for 30 minutes. In addition, 78 mg (2.04 mmol) of sodium borohydride was added to the solution, and the solution was stirred at 55° C. for 30 minutes. Furthermore, 39 mg (1.02 mmol) of sodium borohydride and 0.40 mL of methanol were added to the solution, and the solution was stirred at 55° C. for 30 minutes. To the solution, 1.2 mL of acetone and 7.5 mL of CPME were added, and the solution was washed once with 2.3 mL of water, once with 2.3 mL of a 5% sodium hydrogen carbonate aqueous solution, and twice with 2.3 mL of water. An organic layer was concentrated under reduced pressure. A resulting residue was dissolved in 7.5 mL of heptane, separated, and washed with 3.8 mL of DMF. To a resulting heptane layer, 3.8 mL of heptane was added, and the heptane layer was separated and washed with 3.8 mL of acetonitrile. The heptane layer was separated and washed with the heptane and the acetonitrile once more, and then, the heptane layer was concentrated under reduced pressure to afford 0.32 g of TIPS2-Xtn-OH.

1H-NMR (400 MHz, Benzene-d$_6$) δ1.12-1.16 (m, 42H), 1.24-1.49 (m, 28H), 1.57-1.68 (m, 9H), 3.65-3.72 (m, 8H), 5.57 (d, 1H), 6.77 (dd, 2H), 6.86 (d, 2H), 7.40 (d, 2H)

$^{13}$C-NMR (100 MHz, Benzene-d$_6$) δ12.8 (6C), 18.7 (12C), 26.7 (2C), 26.8 (2C), 29.8-30.5 (12C), 33.9 (2C), 63.3, 64.1 (2C) 8.6 (2C), 102.0 (2C), 10.9 (2C), 116.8 (2C), 131.5 (2C), 152.5 (2C), 160.9 (2C)

Example 2

Synthesis of TIPS2-Xtn-NH$_2$

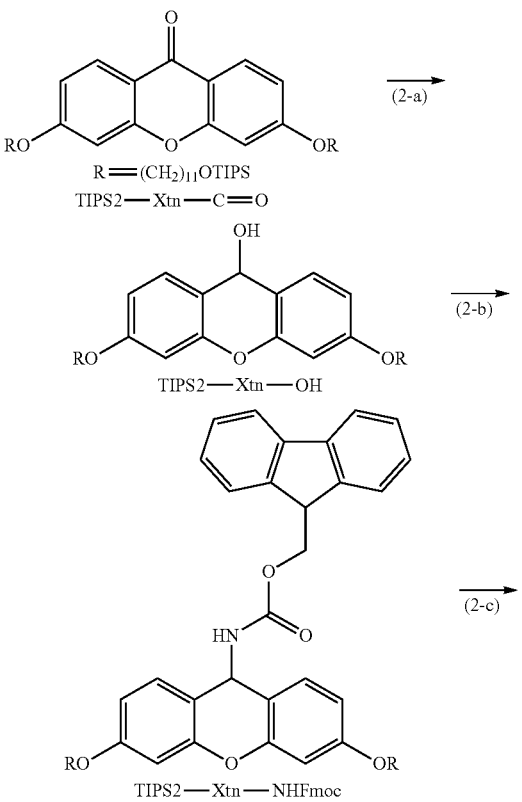

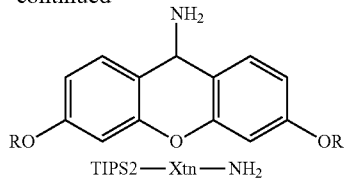

(Hereinafter, TIPS2-Xtn-NHFmoc and TIPS2-Xtn-NH$_2$ represent the structures in the drawing.)

Example (2-a)

In a mixed solution of 180 mL of THF (anhydrous) and 18 mL of methanol, 21.8 g (24.8 mmol) of TIPS2-Xtn-C=O was dissolved, and 7.5 g (198 mmol) of sodium borohydride was added to the mixed solution. The solution was heated to 35° C. and stirred for 10 minutes. In addition, 18 mL of methanol was added to the solution, and the solution was stirred at 35° C. for 1 hour. Furthermore, 3.7 mg (99.0 mmol) of sodium borohydride and 18 mL of methanol were added to the solution, and the solution was stirred at 35° C. for 20 hours and 30 minutes. To the solution, 446 mL of acetone was added, and the reaction solution was concentrated under reduced pressure. A resulting residue was dissolved in 540 mL of toluene and washed 4 times with 360 mL of a 5% sodium hydrogen carbonate aqueous solution. A resulting organic layer was diluted with 18 mL of toluene, and 153 g of anhydrous sodium sulfate was added to the organic layer. The organic layer was thoroughly stirred and then filtered. The filtration residue was washed with 90 mL of toluene to afford a toluene solution containing TIPS2-Xtn-OH.

Example (2-b)

To the toluene solution obtained in the previous step, 7.11 g (29.7 mmol) of Fmoc-NH$_2$ and 82.5 mL of acetic acid were added, and the toluene solution was heated to 50° C. and stirred for 30 minutes. After cooling the reaction solution to 5° C., 194 mL of toluene was added to the solution, and the solution was washed three times with 648 mL of a 5% sodium hydrogen carbonate aqueous solution and twice with 648 mL of water. An organic layer was concentrated under reduced pressure to afford a mixture containing TIPS2-Xtn-NHFmoc.

Example (2-c)

The mixture obtained in the previous step was dissolved in 248 mL of THF, and 13.3 mL (89.1 mmol) of DBU was added to the mixture. The solution was then stirred at room temperature for 30 minutes. The solution was cooled to 5° C., the reaction was quenched with 59.4 mL of 1 N hydrochloric acid, and the solution was concentrated under reduced pressure. A resulting residue was dissolved in 500 mL of heptane, and the residue was washed five times with 500 mL of acetonitrile. A heptane layer was concentrated under reduced pressure, and the resulting residue was purified by silica gel column chromatography (heptane:ethyl acetate:triethylamine=18.75:1.25:1→0:19:1) to afford 8.86 g of TIPS2-Xtn-NH$_2$.

$^1$H-NMR (400 MHz, Benzene-d$_6$) δ1.12-1.16 (m, 42H), 1.24-1.40 (m, 24H), 1.40-1.50 (m, 4H), 1.56-1.68 (m, 10H), 3.65-3.74 (m, 8H), 4.76 (s, 1H), 6.78 (dd, 2H), 6.86 (d, 2H), 7.25 (d, 2H)

$^{13}$C-NMR (100 MHz, Benzene-dδ) δ12.8 (6C), 18.7 (12C), 26.7 (2C), 26.8 (2C), 30.0-30.5 (12C), 33.9 (2C), 46.8, 64.1 (2C), 68.5 (2C), 102.1 (2C), 111.6 (2C), 119.0 (2C), 130.6 (2C), 152.6 (2C), 160.3 (2C)

Example 3

Synthesis of TIPS2-Xtn-OH(C$_8$)

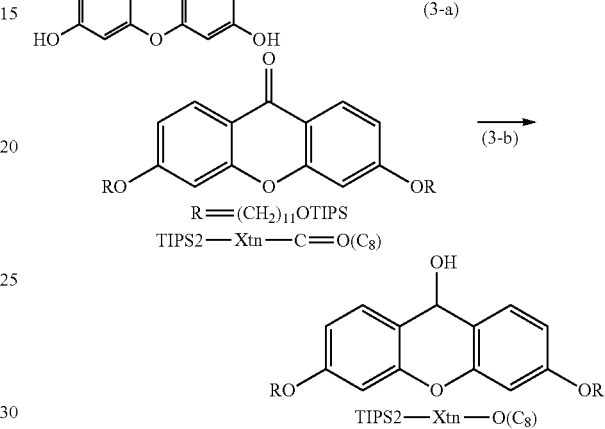

(Hereinafter Br—(CH$_2$)$_8$—OTIPS, TIPS2-Xtn-C=O (C$_8$), and TIPS2-Xtn-OH(C$_8$) represent the structures in the drawing.)

Example (3-a)

1.49 g (4.07 mmol) of Br—(CH$_2$)$_8$—OTIPS, 0.41 g (1.81 mmol) of 3,6-dihydroxyxanthone, and 0.90 g (6.52 mmol) of potassium carbonate were suspended in 12.1 mL of DMF, heated to 85° C., and stirred for 2 hours and 30 minutes. The reaction solution was filtered, and the filtration residue was washed with 25.3 mL of heptane. The filtrate was separated to obtain a heptane layer. To the resulting heptane layer was added 12.1 mL of heptane, and the heptane layer was separated and washed with 12.1 mL of DMF. To the resulting heptane layer, 12.1 mL of heptane was added, and the heptane layer was washed once with 12.1 mL of 1 N hydrochloric acid, once with 12.1 mL of a 5% sodium hydrogen carbonate aqueous solution, and once with 12.1 mL of water. To the resulting heptane layer, 12.1 mL of heptane was added, and the heptane layer was separated and washed twice with 12.1 mL of acetonitrile. The heptane layer was concentrated under reduced pressure, and a resulting residue was purified by silica gel column chromatography (heptane:ethyl acetate=80: 1-0:100) to afford 1.29 g of TIPS2-Xtn-C=O(C$_8$).

$^1$H-NMR (400 MHz, CDCl$_3$) δ1.02-1.08 (m, 42H), 1.33-1.44 (m, 12H), 1.44-1.60 (m, 8H), 1.79-1.89 (m, 4H), 3.68 (t, 4H), 4.06 (t, 4H), 6.83 (d, 2H), 6.91 (dd, 2H), 8.22 (d, 2H)

$^{13}$C-NMR (100 MHz, CDCl$_3$) δ12.2 (6C), 18.2 (12C), 25.9 (2C), 26.1 (2C), 29.1 (2C), 29.5 (4C), 33.1 (2C), 63.6 (2C), 68.8 (2C), 100.8 (2C), 113.3 (2C), 115.8 (2C), 128.2 (2C), 158.2 (2C), 164.4 (2C), 175.7

ESIMS MH+ 797.5

Example (3-b)

In a mixed solution of 6.6 mL of THF (anhydrous) and 0.66 mL of methanol, 0.73 g (0.91 mmol) of TIPS2-Xtn-C=O($C_B$) was dissolved, and 0.28 g (7.30 mmol) of sodium borohydride was added to the mixed solution. The solution was heated to 35° C. and stirred for 10 minutes. To the solution, 0.66 mL of methanol was added, and the solution was stirred at 35° C. for 50 minutes. In addition, 0.14 g (3.65 mmol) of sodium borohydride and 0.66 mL of methanol were added to the solution, and the solution was stirred at 35° C. for 18 hours and 30 minutes. Furthermore, 16.4 mL of acetone and 66.3 mL of hexane were added to the solution, and the solution was washed four times with 36.5 mL of a 5% sodium hydrogen carbonate aqueous solution. To a resulting hexane layer, 3.3 mL of hexane and 5.1 g of anhydrous sodium sulfate were added, and the hexane layer was thoroughly stirred and then filtered. The filtration residue was washed with 3.3 mL of hexane, and the filtrate was concentrated under reduced pressure to afford 0.72 g of TIPS2-Xtn-OH($C_8$).

1H-NMR (400 MHz, Benzene-$d_6$) δ 1.12-1.16 (m, 42H), 1.22-1.37 (m, 12H), 1.37-1.45 (m, 4H), 1.52-1.66 (m, 9H), 3.67 (t, 8H), 5.57 (d, 1H), 6.76 (dd, 2H), 6.85 (d, 2H), 7.40 (d, 2H)

$^{13}$C-NMR (100 MHz, Benzene-$d_6$) δ12.8 (6C), 18.7 (12C), 26.6 (2C), 26.7 (2C), 29.9 (2C), 30.1 (2C), 30.2 (2C), 33.8 (2C), 63.4, 64.1 (2C), 68.5 (2C), 102.0 (2C), 111.9 (2C), 116.8 (2C), 131.5 (2C), 152.5 (2C), 160.9 (2C)

ESIMS MNa+ 821.5

Example 4

Synthesis of TBDPS2-Xtn-OH

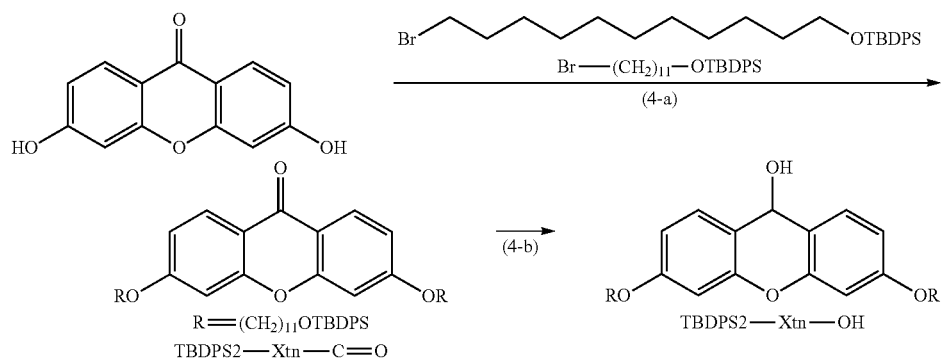

(Hereinafter, Br—(CH$_2$)$_{11}$-OTBDPS, TBDPS2-Xtn-C=O, and TBDPS2-Xtn-OH represent the structures in the drawing.)

Example (4-a)

1.16 g (2.38 mmol) of Br—(CH$_2$)$_{11}$-OTBDPS, 0.24 g (1.06 mmol) of 3,6-dihydroxyxanthone, and 0.53 g (3.80 mmol) of potassium carbonate were suspended in 7.0 mL of DMF, heated to 85° C., and stirred for 3 hours. The reaction solution was filtered, and the filtration residue was washed with 14.8 mL of heptane. The filtration was separated to obtain a heptane layer. To the resulting heptane layer was added 7.0 mL of heptane, and the heptane layer was separated and washed with 7.0 mL of acetonitrile. To the resulting heptane layer, 7.0 mL of heptane was added, and the heptane layer was washed once with 7.0 mL of 1 N hydrochloric acid, once with 7.0 mL of a 5% sodium hydrogen carbonate aqueous solution, and once with 7.0 mL of water. To the resulting heptane layer, 7.0 mL of heptane was added, and the heptane layer was separated and washed twice with 7.0 mL of acetonitrile. The heptane layer was concentrated under reduced pressure, and a resulting residue was purified by silica gel column chromatography (heptane:ethyl acetate=80: 1-0:100) to afford 0.67 g of TBDPS2-Xtn-C=O.

1H-NMR (400 MHz, CDCl$_3$) δ1.05 (s, 18H), 1.24-1.42 (m, 24H), 1.42-1.63 (m, 8H), 1.77-1.89 (m, 4H), 3.66 (t, 4H), 4.07 (t, 4H), 6.84 (d, 2H), 6.92 (dd, 2H), 7.30-7.44 (m, 12H), 7.60-7.70 (m, 8H), 8.23 (d, 2H)

$^{13}$C-NMR (100 MHz, CDCl$_3$) δ19.4 (2C), 25.9 (2C), 26.1 (2C), 27.0 (6C), 29.2-29.7 (12C), 32.7 (2C), 64.2 (2C), 68.8 (2C), 100.8 (2C), 113.4 (2C), 5.8 (2C), 127.7 (8C), 128.3 (2C), 129.6 (4C), 134.3 (4C), 135.7 (8C), 158.2 (2C), 164.4 (2C), 175.7

ESIMS MNa+ 1067.5

Example (4-b)

In a mixed solution of 2.3 mL of THF (anhydrous) and 0.23 mL of methanol, 0.33 g (0.32 mmol) of TBDPS2-Xtn-C=O was dissolved, and 95 mg (2.52 mmol) of sodium borohydride was added to the mixed solution. The solution was heated to 35° C. and stirred for 10 minutes. To the solution, 0.23 mL of methanol was added, and the solution was stirred at 35° C. for 50 minutes. In addition, 48 mg (1.26 mmol) of sodium borohydride and 0.23 mL of methanol were added to the solution, and the solution was stirred at 35° C. for 18 hours and 30 minutes, then, cooled to room temperature and stirred for 49 hours and 30 minutes. Furthermore, 5.7 mL of acetone and 22.9 mL of hexane were added to the solution, and the solution was washed four times with 12.6 mL of a 5% sodium hydrogen carbonate aqueous solution. To a resulting hexane layer, 1.2 mL of hexane and 2.3 g of anhydrous sodium sulfate were added, and the hexane layer was thoroughly stirred and then filtered. The filtration residue was washed with 1.2 mL of hexane, and the filtrate was concentrated under reduced pressure to afford 0.31 g of TBDPS2-Xtn-OH.

1H-NMR (400 MHz, Benzene-$d_6$) δ1.20 (s, 18H), 1.22-1.29 (m, 24H), 1.31-1.43 (m, 4H), 1.53-1.69 (m, 9H), 3.65-3.73 (m, 8H), 5.57 (d, H), 6.77 (dd, 2H), 6.85 (d, 2H), 7.21-7.27 (m, 12H), 7.40 (d, 2H), 7.77-7.83 (m, 8H)

ESIMS MNa+ 1069.2

Example 5

Synthesis of TIPS2-Xtn-OH(C$_{14}$)

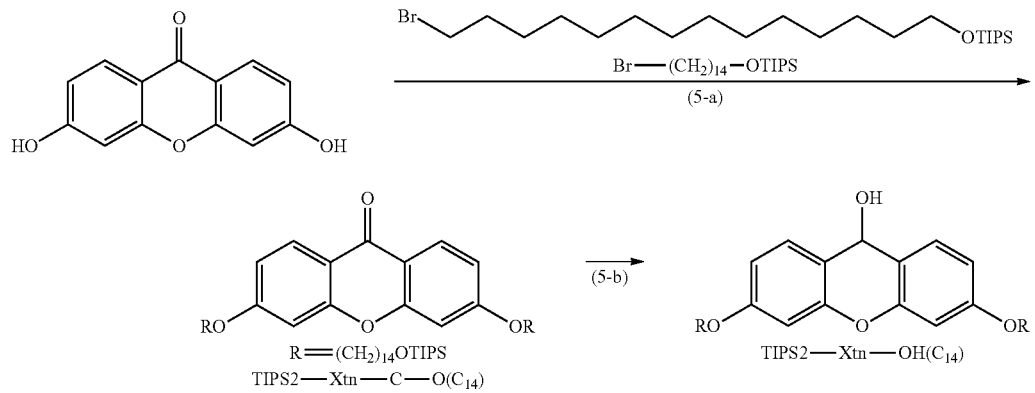

(Hereinafter, Br—(CH$_2$)$_{14}$—OTIPS, TIPS2-Xtn-C=O (C$_{14}$), and TIPS2-Xtn-OH(C$_{14}$) represent the structures in the drawing.)

Example (5-a)

1.53 g (3.34 mmol) of Br—(CH$_2$)$_{14}$—OTIPS, 0.34 g (1.51 mmol) of 3,6-dihydroxyxanthone, and 0.75 g (5.43 mmol) of potassium carbonate were suspended in 10.1 mL of DMF, heated to 85° C., and stirred for 3 hours. The reaction solution was filtered, and the filtration residue was washed with 21.1 mL of heptane. The filtrate was separated to obtain a heptane layer. To the resulting heptane layer was added 10.1 mL of heptane, and the heptane layer was separated and washed with 10.1 mL of DMF. To the resulting heptane layer, 10.1 mL of heptane was added, and the heptane layer was washed once with 10.1 mL of 1 N hydrochloric acid, once with 10.1 mL of a 5% sodium hydrogen carbonate aqueous solution, and once with 10.1 mL of water. To the resulting heptane layer, 10.1 mL of heptane was added, and the heptane layer was separated and washed twice with 10.1 mL of acetonitrile. The heptane layer was concentrated under reduced pressure to afford 1.34 g of TIPS2-Xtn-C=O(C$_{14}$).

$^1$H-NMR (400 MHz, CDCl$_3$) δ1.04-1.08 (m, 42H), 1.23-1.42 (m, 40H), 1.43-1.58 (m, 4H), 1.79-1.89 (m, 4H), 3.66 (t, 4H), 4H), 4.06 (t, 4H), 6.83 (d, 2H), 6.91 (dd, 2H), 8.22 (d, 2H)

ESIMS MH+ 965.8

Example (5-b)

TIPS2-Xtn-OH(C$_{14}$) was Obtained in a Manner Similar to TIPS2-Xtn-OH (C$_8$)

$^1$H-NMR (400 MHz, Benzene-d$_6$) δ1.12-1.16 (m, 42H), 1.23-1.49 (m, 40H), 1.57-1.69 (m, 9H), 3.66-3.73 (m, 8H), 5.57 (d, 1H), 6.77 (dd, 2H), 6.86 (d, 2H), 7.40 (d, 2H)

ESIMS MNa+ 990.2

Example 6

Synthesis of TIPS2-Xtn-OH(C$_8$OC$_2$)

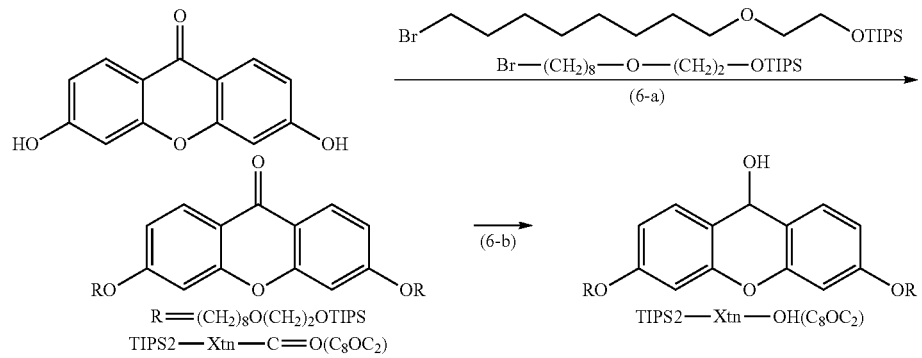

(Hereinafter, Br—(CH$_2$)$_8$—O—(CH$_2$)$_2$—OTIPS, TIPS2-Xtn-C=O(C$_8$OC$_2$), and TIPS2-Xtn-OH(C$_8$OC$_2$) represent the structures in the drawing.)

Example (6-a)

0.95 g (2.31 mmol) of Br—$(CH_2)_8$—O—$(CH_2)_2$-OTIPS, 0.23 g (1.03 mmol) of 3,6-dihydroxyxanthone, and 0.57 g (4.11 mmol) of potassium carbonate were suspended in 6.8 mL of DMF, heated to 85° C., and stirred for 2 hours and 40 minutes. The reaction solution was filtered, and the filtration residue was washed with 14.4 mL of heptane. The filtrate was separated to obtain a heptane layer. To the resulting heptane layer was added 6.8 mL of heptane. The heptane layer was separated and washed with 6.8 mL of DMF. To the resulting heptane layer, 6.8 mL of heptane was added, and the heptane layer was washed once with 6.8 mL of 1 N hydrochloric acid, once with 6.8 mL of a 5% sodium hydrogen carbonate aqueous solution, and once with 6.8 mL of water. To the resulting heptane layer, 6.8 mL of heptane was added, and the heptane layer was separated and washed with 6.8 mL of acetonitrile. The heptane layer was separated and washed once more with the heptane and the acetonitrile, and then, the heptane layer was concentrated under reduced pressure. A resulting residue was purified by silica gel column chromatography (heptane:ethyl acetate=40:1-0:100) to yield 0.24 g of TIPS2-Xtn-C=O($C_8OC_2$).

$^1$H-NMR (400 MHz, CDCl$_3$) δ1.03-1.07 (m, 42H), 1.25-1.43 (m, 12H), 1.43-1.53 (m, 4H), 1.53-1.62 (m, 4H), 1.77-1.89 (m, 4H), 3.48 (t, 4H), 3.52 (t, 4H), 3.83 (t, 4H), 4.06 (t, 4H), 6.82 (d, 2H), 6.91 (dd, 2H), 8.21 (d, 2H)

ESIMS MH+ 885.6

Example (6-b)

TIPS2-Xtn-OH(COC$_2$) was Obtained in a Manner Similar to TIPS2-Xtn-OH(C$_8$)

$^1$H-NMR (400 MHz, Benzene-d$_6$) δ1.11-1.15 (m, 42H), 1.20-1.29 (m, 8H), 1.29-1.42 (m, 8H), 1.54-1.66 (m, 9H), 3.39 (t, 4H), 3.49 (t, 4H), 3.68 (t, 4H), 3.83 (t, 4H), 5.58 (d, 1H), 6.76 (dd, 2H), 6.85 (d, 2H), 7.41 (d, 2H)

ESIMS MNa+ 909.8

Example 7

Synthesis of TIPS2-Xtn-OH(C$_{10}$—CONH—C$_2$)

(Hereinafter, Br—$(CH_2)_{10}$—CONH—$(CH_2)_2$—OTIPS, TIPS2-Xtn-C=O (C$_{10}$—CONH—C$_2$), and TIPS2-Xtn-OH (C$_{10}$—CONH—C$_2$) represent the structures in the drawing.)

Example (7-a)

1.63 g (3.50 mmol) of Br—$(CH_2)_{10}$—CONH—$(CH_2)_2$—OTIPS, 0.29 g (1.25 mmol) of 3,6-dihydroxyxanthone, and 0.69 g (5.00 mmol) of potassium carbonate were suspended in 8.3 mL of DMF, heated to 115° C., and stirred for 2 hours. The reaction solution was filtered. To a filtrate, 25 mL of water was added to undergo slurry washing, and a precipitate was collected by filtration. The slurry washing with water and the filtration were carried out once more. To the resulting precipitate, 25 mL of acetonitrile was added to undergo slurry washing, and a precipitate was collected by filtration. The slurry washing with acetonitrile and the filtration were carried out once more. The resulting precipitate was dried under reduced pressure to obtain 0.99 g of TIPS2-Xtn-C=O(C$_{10}$—CONH—C$_2$).

$^1$H-NMR (400 MHz, CDCl$_3$). 03-1.08 (m, 42H), 1.25-1.42 (m, 20H), 1.43-1.53 (m, 4H), 1.56-1.68 (m, 4H), 1.79-1.88 (m, 4H), 2.18 (t, 4H), 3.40 (q, 4H), 3.76 (t, 4H), 4.06 (t, 4H), 5.89 (t, 2H), 6.83 (d, 2H), 6.91 (dd, 2H), 8.21 (d, 2H)

ESIMS MNa+ 1017.7

Example (7-b)

In a mixed solution of 1.5 mL of THF (anhydrous) and 0.15 mL of methanol, 0.21 g (0.21 mmol) of TIPS2-Xtn-C=O(C$_{10}$—CONH—C$_2$) was dissolved, and 64 mg (1.69 mmol) of sodium borohydride was added to the mixed solution. The solution was heated to 35° C. and stirred for 10 minutes. To the solution, 0.15 mL of methanol was added, and the solution was stirred at 35° C. for 50 minutes. In addition, 32 mg (0.84 mmol) of sodium borohydride and 0.15 mL of methanol were added to the solution, and the solution was stirred at 35° C. for 21 hours and 10 minutes. Furthermore, 3.8 mL of acetone and 15.3 mL of ethyl acetate were added to the solution, and the solution was washed four times with 8.4 mL of a 5% sodium hydrogen carbonate aqueous solution. To a resulting organic layer, 0.8 mL of ethyl acetate and 1.47 g of anhydrous sodium sulfate were added, and the organic layer was thoroughly stirred and then filtered. The filtration residue was washed with 0.8 mL of ethyl acetate, and the filtrate was concentrated under reduced pressure to afford 0.21 g of TIPS2-Xtn-OH(C$_{10}$—CONH—C$_2$).

ESIMS MNa+ 1019.6

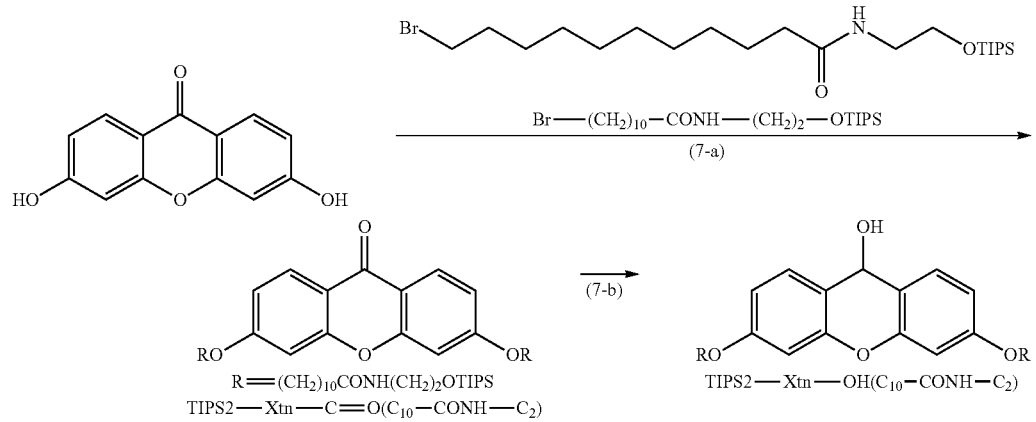

Example 8

Synthesis of TIPS3-Xtn-NH$_2$

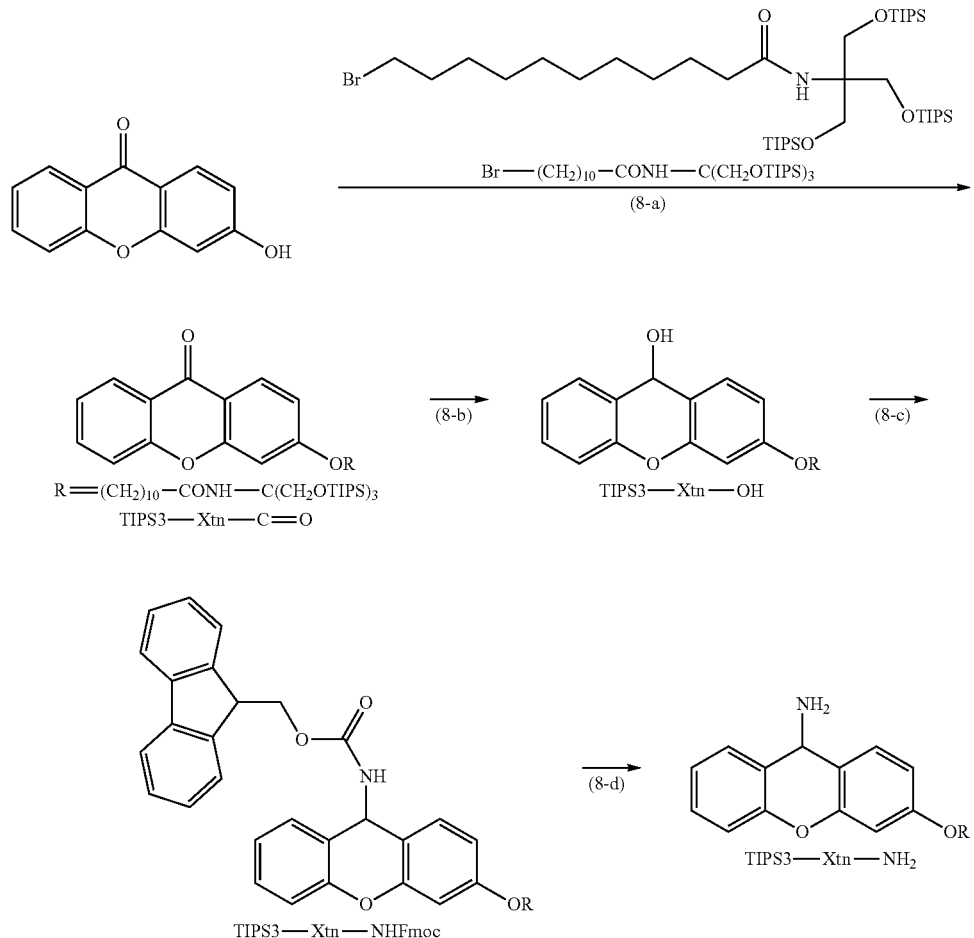

(Hereinafter, Br—(CH$_2$)$_{10}$—CONH—C(CH$_2$OTIPS)$_3$, TIPS3-Xtn-C=O, TIPS3-Xtn-OH, TIPS3-Xtn-NHFmoc, and TIPS3-Xtn-NH$_2$ represent the structures in the drawing.)

Example (8-a)

9.01 g (10.8 mmol) of Br—(CH$_2$)$_{10}$—CONH—C(CH$_2$OTIPS)$_3$, 2.86 g (12.9 mmol) of 3-hydroxanthene-9-one, and 2.69 g (19.4 mmol) of potassium carbonate were suspended in 72 mL of DMF, heated to 120° C., and stirred for 5 hours. The reaction solution was filtered, and the filtration residue was washed with 151 mL of heptane. The filtrate was separated to obtain a heptane layer. To the resulting heptane layer was added 72 mL of heptane The heptane layer was separated and washed with 72 mL of DMF. 72 mL of DMF was further added to the heptane layer, and the heptane layer was separated and washed twice. The resulting heptane layer was washed once with 72 mL of water. The heptane layer was concentrated under reduced pressure to afford 5.68 g of TIPS3-Xtn-C=O.

$^1$H-NMR (400 MHz, CDCl$_3$) δ$^1$H-NMR (400 MHz, CDCl$_3$) δ1.02-1.08 (m, 63H), 1.24-1.39 (m, 10H), 1.44-1.62 (m, 4H), 1.85 (quin., 2H), 2.09 (t, 2H), 4.04 (s, 6H), 4.08 (t, 2H), 5.75 (s, 1H), 6.87 (d, 1H), 6.94 (dd, 1H), 7.37 (t, 1H), 7.45 (d, 1H), 7.66-7.72 (m, 1H), 8.24 (d, 1H), 8.33 (dd, 1H)

Example (8-b)

In a mixed solution of 4.0 mL of THF (anhydrous) and 0.8 mL of methanol, 0.70 g (0.73 mmol) of TIPS3-Xtn-C=O was dissolved, and 0.22 g (5.81 mmol) of sodium borohydride was added to the mixed solution. The solution was heated to 35° C. and stirred for 4 hours. The reaction was quenched with 0.86 mL of acetone, and the solution was concentrated under reduced pressure. A resulting residue was dissolved in 13 mL of toluene, and the residue was washed twice with 3.9 mL of a 5% sodium hydrogen carbonate aqueous solution and twice with 3.9 mL of water to afford a toluene solution containing TIPS3-Xtn-OH.

Example (8-c)

To the toluene solution obtained in the previous step, 0.21 g (0.87 mmol) of 9-fluorenylmethyl carbamate, 0.42 mL of acetic acid, and 1.72 g of molecular sieves 4 Å were added, and the solution was stirred at 50° C. for 3 hours and 30 minutes. The reaction solution was filtered, diluted with 10 mL of toluene, and washed once with 40 mL of a 5% sodium hydrogen carbonate aqueous solution, once with 30 mL of 5% sodium hydrogen carbonate aqueous, and once with 20 mL of water. The solution was concentrated under reduced pressure to afford a mixture containing TIPS3-Xtn-NHF-moc.

Example (8-d)

The mixture obtained in the previous step was dissolved in 6.9 mL of THF, and 0.15 mL (1.03 mmol) of DBU was added to the mixture, and the mixture was stirred at room temperature for 1 hour. The solution was concentrated under reduced pressure, and a residue was dissolved in 21.0 mL of heptane, and separated and washed with 7.0 mL of DMF. To a resulting heptane layer, 7.0 mL of heptane was added. The heptane layer was separated and washed twice with 7.0 mL of DMF. To the heptane layer, 7.0 mL of heptane was added, and the heptane layer was separated and washed with 7.0 mL of 50% aqueous acetonitrile. The heptane layer was separated and washed with the heptane and the 50% aqueous acetonitrile once more. To the resulting heptane layer, 7.0 mL of heptane was added, and the heptane layer was separated and washed with 7.0 mL of acetonitrile. After separating and washing the heptane layer once more with the heptane and the acetonitrile, the heptane layer was concentrated under reduced pressure, and a resulting residue was purified by silica gel column chromatography (heptane:ethyl acetate:triethylamine=17.8:1.2:1-0:19:1) to afford 0.44 g of TIPS3-Xtn-NH$_2$.

$^1$H-NMR (400 MHz, Benzene-d$_6$) δ1.14-1.18 (m, 63H), 1.22-1.40 (m, 14H), 1.63 (quin., 2H), 1.75 (quin., 2H), 2.20 (t, 2H), 3.69 (t, 2H), 4.43 (s, 6H), 4.70 (s, 1H), 5.91 (s, 1H), 6.78 (dd, 1H), 6.82 (d, 1H), 6.93 (td, 1H), 7.04 (td, 1H), 7.14 (dd, 1H), 7.22 (d, 1H), 7.28 (dd, 1H)

Example 9

Synthesis of TIPS3-Xtn-OH(6-OMe)

(Hereinafter, TIPS3-Xtn-C═O(6-OMe) and TIPS3-Xtn-OH(6-OMe) represent the structures in the drawing.)

Example (9-a)

0.40 g (0.48 mmol) of Br—(CH$_2$)$_{10}$—CONH—C(CH$_2$OTIPS)$_3$, 0.22 g (0.91 mmol) of 3-hydroxy-6-methoxyxanthone, and 0.20 g (1.43 mmol) of potassium carbonate were suspended in 3.2 mL of DMF, heated to 115° C., and stirred for 3 hours and 20 minutes. The reaction solution was filtered, and the filtration residue was washed with 4.8 mL of heptane. The filtrate was separated to obtain a heptane layer. To the resulting heptane layer was added 2.4 mL of heptane, and the heptane layer was separated and washed with 2.4 mL of DMF. To the resulting heptane layer, 2.4 mL of heptane was added, and the heptane layer was washed once with 2.4 mL of 1 N hydrochloric acid, once with 2.4 mL of a 5% sodium hydrogen carbonate aqueous solution, and once with 2.4 mL of water. To the resulting heptane layer, 2.4 mL of heptane was added, and the heptane layer was separated and washed with 2.4 mL of acetonitrile. The heptane layer was separated and washed once more with the heptane and the acetonitrile, and then, the heptane layer was concentrated under reduced pressure to afford 0.27 g of TIPS3-Xtn-C═O(6-OMe).

$^1$H-NMR (400 MHz, CDCl$_3$) δ1.00-1.07 (m, 63H), 1.20-1.40 (m, 10H), 1.48 (quin., 2H), 1.57 (quin., 2H), 1.84 (quin., 2H), 2.09 (t, 2H), 3.92 (s, 3H), 4.02-4.09 (m, 8H), 5.75 (s, 1H), 6.84 (dd, 2H), 6.89-6.94 (m, 2H), 8.20-8.25 (m, 2H)

ESIMS MH+ 998.8

Example (9-b)

TIPS3-Xtn-OH(6-OMe) was Obtained in a Manner Similar to TIPS2-Xtn-OH (C$_8$)

$^1$H-NMR (400 MHz, Benzene-d) δ1.15-1.19 (m, 63H), 1.20-1.41 (m, 12H), 1.55-1.80 (m, 5H), 2.19 (t, 2H), 3.30 (s, 3H), 3.70 (t, 2H), 4.42 (s, 6H), 5.56 (d, 1H), 5.91 (s, 1H), 6.68 (dd, 1H), 6.75-6.80 (m, 2H), 6.85 (d, 1H), 7.36-7.43 (m, 2H)

ESIMS MNa+ 1022.7

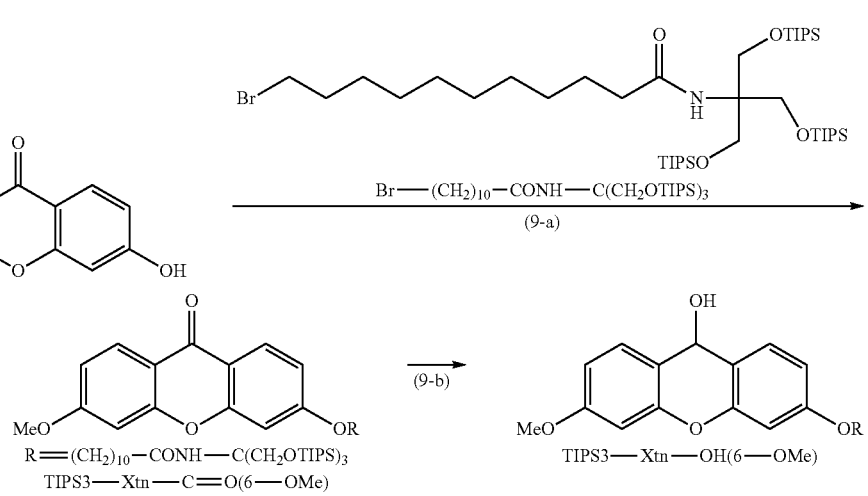

Example 10

Synthesis of TIPS4-Xtn-OH ($C_{10}$—CONH—CH$(CH_2)_2$)

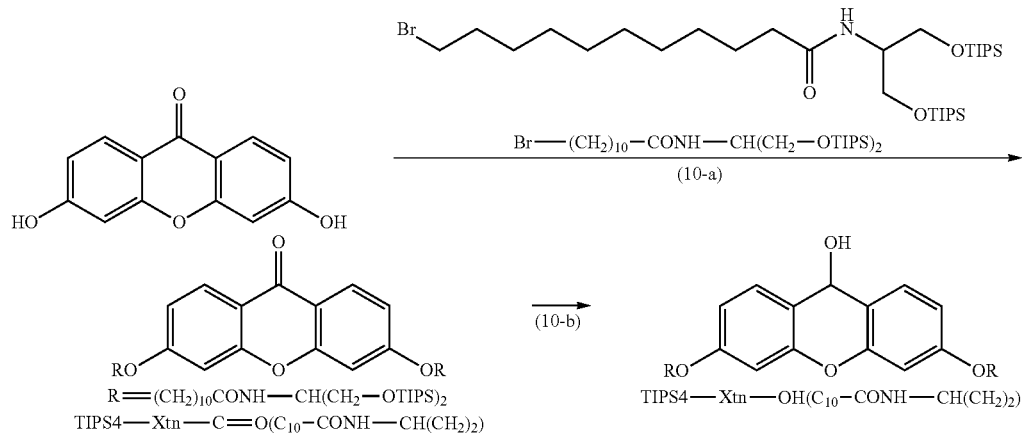

(Hereinafter, Br—$(CH_2)_{10}$—CONH—CH$(CH_2$—OTIPS$)_2$, TIPS4-Xtn-C=O ($C_{10}$—CONH—CH$(CH_2)$ 2), and TIPS4-Xtn-OH ($C_{10}$—CONH—CH$(CH_2)_2$) represent the structures in the drawing.)

Example (10-a)

1.53 g (2.35 mmol) of Br—$(CH_2)_{10}$—CONH—CH$(CH_2$—OTIPS$)_2$, 0.19 g (0.84 mmol) of 3,6-dihydroxyxanthone, and 0.47 g (3.36 mmol) of potassium carbonate were suspended in 5.6 mL of DMF, heated to 115° C., and stirred for 3 hours and 30 minutes. The reaction solution was filtered, and the filtration residue was washed with 11.8 mL of heptane. The filtrate was separated to obtain a heptane layer. To the resulting heptane layer was added 5.6 mL of heptane, and the heptane layer was separated and washed with 5.6 mL of DMF. To the resulting heptane layer, 5.6 mL of heptane was added, and the heptane layer was washed once with 5.6 mL of 1 N hydrochloric acid, once with 5.6 mL of a 5% sodium hydrogen carbonate aqueous solution, and once with 5.6 mL of water. To the resulting heptane layer, 5.6 mL of heptane was added, and the heptane layer was separated and washed with 5.6 mL of acetonitrile. The heptane layer was separated and washed once more with the heptane and the acetonitrile. The heptane layer was concentrated under reduced pressure to afford 0.74 g of TIPS4-Xtn-C=O($C_{10}$—CONH—CH$(CH_2)_2$).

$^1$H-NMR (400 MHz, CDCl$_3$) δ1.04-1.08 (m, 84H), 1.22-1.42 (m, 20H), 1.43-1.52 (m, 4H), 1.56-1.66 (m, 4H), 1.79-1.88 (m, 4H), 2.16 (t, 4H), 3.64-3.70 (m, 4H), 3.86-3.91 (m, 4H), 3.94-4.04 (m, 2H), 4.06 (t, 4H), 5.84 (d, 2H), 6.83 (d, 2H), 6.91 (dd, 2H), 8.22 (d, 2H)

ESIMS MH+ 1367.9

Example (10-b)

TIPS4-Xtn-OH($C_{10}$—CONH—CH$(CH_2)_2$) was Obtained in a Manner Similar to TIPS2-Xtn-OH ($C_8$)

1H-NMR (400 MHz, Benzene-d$_6$) δ1.10-1.15 (m, 84H), 1.20-1.41 (m, 24H), 1.60-1.73 (m, 9H), 2.03 (t, 4H), 3.68-3.77 (m, 8H), 4.01-4.07 (m, 4H), 4.27-4.36 (m, 2H), 5.61 (d, 1H), 5.71 (d, 2H), 6.78 (dd, 2H), 6.87 (d, 2H), 7.44 (d, 2H)

ESIMS MNa+ 1391.7

Example 11

Synthesis of TIPS6-Xtn-NH$_2$

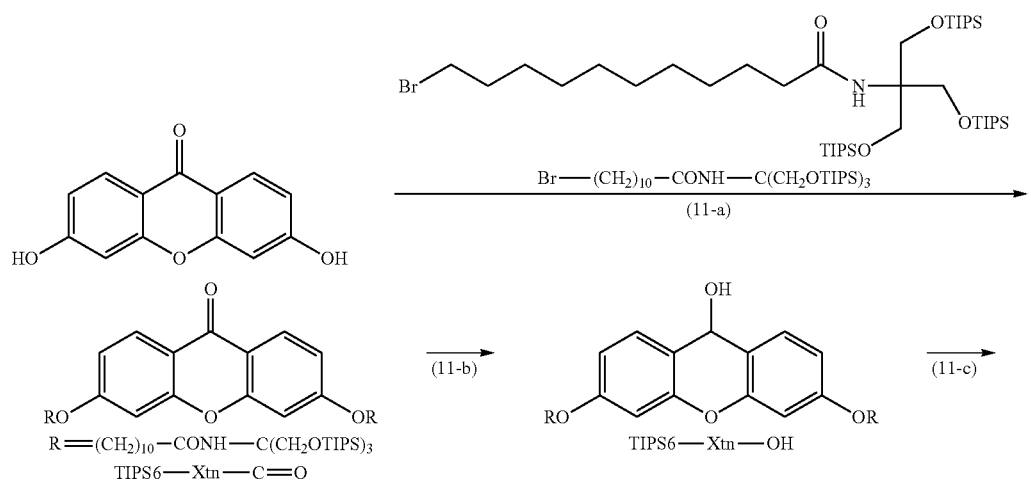

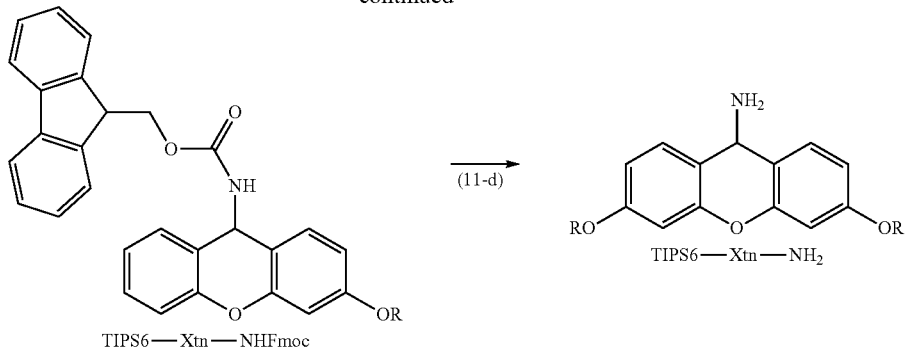

(Hereinafter, TIPS6-Xtn-C=O, TIPS6-Xtn-OH, TIPS6-Xtn-NHFmoc, and TIPS6-Xtn-NH₂ represent the structures in the drawing.)

Example (11-a)

8.18 g (9.77 mmol) of Br—(CH$_2$)$_{10}$—CONH—C(CH$_2$OTIPS)$_3$, 0.68 g (3.00 mmol) of 3,6-dihydroxyxanthone, and 1.50 g (10.9 mmol) of potassium carbonate were suspended in 20.0 mL of DMF, heated to 90° C., and stirred for 9.5 hours. The reaction solution was filtered, and the filtration residue was washed with 42 mL of heptane. The filtrate was separated to obtain a heptane layer. To the resulting heptane layer was added 20 mL of heptane was added. The heptane layer was separated and washed with 20 mL of DMF. The heptane layer was separated and washed with the heptane and the DMF once more. To the resulting heptane layer, 20 mL of heptane was added, and the heptane layer was washed once with 20 mL of 1 N hydrochloric acid, once with 20 mL of a 5% sodium hydrogen carbonate aqueous solution, and twice with 20 mL of water. 20 mL of Heptane was added to the resulting heptane layer, and the heptane layer was separated and washed once with 20 mL of DMF and twice with 20 mL of acetonitrile. The heptane layer was concentrated under reduced pressure, and a resulting residue was purified by silica gel column chromatography (heptane:ethyl acetate=35: 1-10:1) to afford 4.13 g of TIPS6-Xtn-C=O.

$^1$H-NMR (400 MHz, Chloroform-d$_1$) δ1.00-1.12 (m, 126H), 1.25-1.37 (m, 20H), 1.47 (quin, 4H), 1.57 (quin, 4H), 1.83 (quin, 4H), 2.08 (t, 4H), 4.03 (s, 12H), 4.05 (t, 4H), 5.74 (s, 2H), 6.82 (dd, 2H), 6.88-6.92 (m, 2H), 8.21 (dd, 2H)

Example (11-b)

In a mixed solution of 12.5 mL of THF (anhydrous) and 3.8 mL of methanol, 3.00 g (1.72 mmol) of TIPS6-Xtn-C=O was dissolved, and 0.79 g (20.8 mmol) of sodium borohydride was added to the mixed solution. The solution was stirred at room temperature for 15 hours. The reaction was quenched with 47.0 mL of acetone, and the solution was concentrated under reduced pressure. A resulting residue was dissolved in 37.6 mL of toluene and washed with 25.1 mL of a 5% sodium hydrogen carbonate aqueous solution. In addition, the residue was washed three times with 25.1 mL of the 5% sodium hydrogen carbonate aqueous solution to afford a toluene solution of a mixture containing TIPS 6-Xtn-OH.

$^1$H-NMR (400 MHz, Benzene-d) 61.07-1.13 (m, 126H), 1.14-1.26 (m, 20H), 1.34-1.37 (m, 4H), 1.58 (quin, 4H), 1.68 (quin, 4H), 2.13 (t, 4H), 3.64 (t, 4H), 4.36 (s, 12H), 5.52-5.55 (d, 1H), 5.85 (s, 2H), 6.72 (dd, 2H), 6.80 (d, 2H), 7.37 (d, 2H)

Example (11-c)

To the toluene solution obtained in the previous step, 0.50 g (2.10 mmol) of 9-fluorenylmethyl carbamate, 5.74 mL of acetic acid, and 0.49 g of molecular sieves 4 Å were added, and the solution was stirred at room temperature for 6 hours. After the reaction solution was cooled to 5° C., 45.1 mL of a saturated sodium hydrogen carbonate aqueous solution was added to the solution, and the solution was stirred for 30 minutes. The reaction solution was filtered, and the filtration residue was washed with 13.5 mL of toluene and separated. Then, the filtrate was washed once with 45.1 mL of a saturated sodium hydrogen carbonate aqueous solution, once with 45.1 mL of a 5% sodium hydrogen carbonate aqueous solution, and twice with 45.1 mL of water. An organic layer was concentrated under reduced pressure to afford a mixture containing TIPS2-Xtn-NHFmoc.

Example (11-d)

The mixture obtained in the previous step was dissolved in 12.7 mL of THF, and 0.69 mL (4.58 mmol) of DBU was added to the mixture, and the mixture was stirred at room temperature for 1 hour. The reaction solution was cooled to 5° C., the reaction was quenched with 3.1 mL of 1 N hydrochloric acid, and the solution was concentrated under reduced pressure. A resulting residue was dissolved in 25.5 mL of heptane, and the solution was washed six times with 25.5 mL of acetonitrile. A heptane layer was concentrated under reduced pressure, and the resulting residue was purified by silica gel column chromatography (heptane:ethyl acetate:triethylamine=18.75:1.25:1→0:19:1) to afford 1.37 g of TIPS6-Xtn-NH$_2$.

$^1$H-NMR (400 MHz, Benzene-d$_6$) δ 1.06-1.14 (m, 126H), 1.14-1.19 (m, 20H), 1.25-1.32 (m, 4H), 1.58 (quin, 4H), 1.69 (quin, 4H), 2.13 (t, 4H), 3.65 (t, 4H), 4.37 (s, 12H), 4.69 (s, 1H), 5.84 (s, 2H), 6.73 (dd, 2H), 6.81 (d, 2H), 7.19 (d, 2H)

Example 12

Synthesis and Deprotection of Fmoc-Cys(TIPS2-Xtn)-NH$_2$

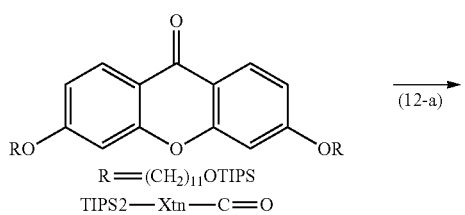

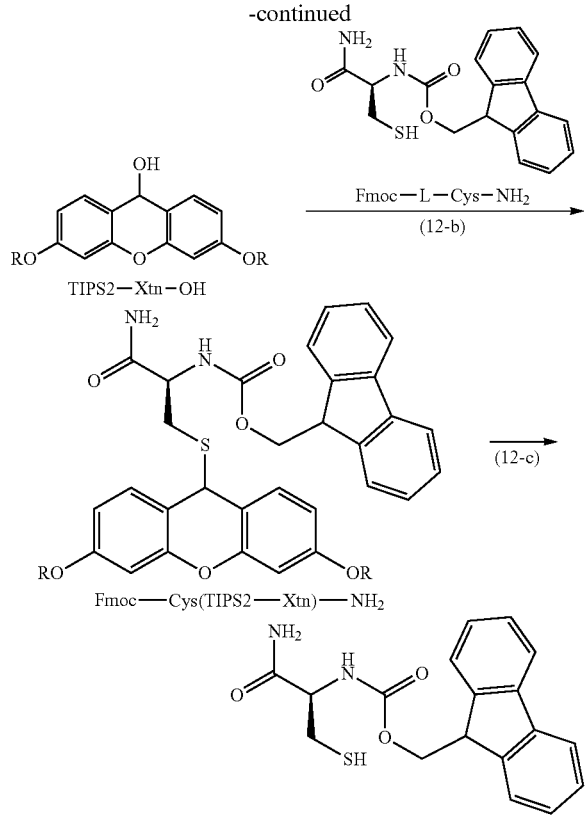

(Hereinafter, Fmoc-L-Cys-NH$_2$ and Fmoc-Cys(TIPS2-Xtn)-NH$_2$ represent the structures in the drawing.)

Example (12-a)

In a mixed solution of 0.83 mL of THF (anhydrous) and 83 µL of methanol, 0.10 g (0.12 mmol) of TIPS2-Xtn-C=O was dissolved, and 35 mg (0.92 mmol) of sodium borohydride was added to the mixed solution. The solution was heated to 35° C. and stirred for 10 minutes. To the solution, 83 µL of methanol was further added, and the was stirred at 35° C. for 50 minutes. In addition, 17 mg (0.46 mmol) of sodium borohydride and 83 µL of methanol were added to the solution, and the solution was stirred at 35° C. for 20 hours and 45 minutes. Furthermore, 2.0 mL of acetone was added to the solution, and the reaction solution was concentrated under reduced pressure. A resulting residue was dissolved in 2.5 mL of toluene and washed 4 times with 1.7 mL of a 5% sodium hydrogen carbonate aqueous solution. A resulting organic layer was diluted with 0.1 mL of toluene, and 0.71 g of anhydrous sodium sulfate was added to the organic layer. The organic layer was thoroughly stirred and filtered, and the filtration residue was washed with 0.4 mL of toluene to afford a toluene solution containing TIPS2-Xtn-OH.

Example (12-b)

To the toluene solution obtained in the previous step, 43 mg (0.13 mmol) of Fmoc-L-Csy-NH$_2$, 39 mg of molecular sieves 4 Å, and 0.38 mL of acetic acid were added, and the solution was stirred at 25° C. for 1 hour and 30 minutes. After the reaction solution was cooled to 5° C., and the reaction was quenched with 4.5 mL of a saturated sodium hydrogen carbonate aqueous solution. To the solution, 3.0 mL of toluene were added, and the solution was washed twice with 4.5 mL of a saturated sodium hydrogen carbonate aqueous solution and once with 3.0 mL of water. An organic layer was concentrated under reduced pressure.

To a resulting residue, 3.1 mL of methanol was added, and the residue was cooled to 5° C. and underwent slurry washing, and a precipitate was collected by filtration. The slurry washing with methanol and the filtration were repeated twice. The resulting precipitate was dissolved in a mixed solvent including 30 mL of heptane and 4.5 mL of CPME, and the resultant was washed three times with 30 mL of acetonitrile. A heptane layer was concentrated under reduced pressure to afford 76 mg of Fmoc-Cys(TIPS2-Xtn)-NH$_2$.

ESIMS MNa+ 1229.8

Example (12-c)

57 mg (0.05 mmol) of Fmoc-Cys(TIPS2-Xtn)-NH$_2$ was dissolved in 0.76 mL of dichloromethane. To the solution, 47 µL (0.29 mmol) of 3,6-dioxa-1,8-octanedithiol, 47 µL (0.22 mmol) of triisopropylsilane, and 94 µL (1.23 mmol) of trifluoroacetic acid were added, and the mixture was stirred at room temperature for 2 hours. The reaction solution was concentrated under reduced pressure, and a residue was dropped to 3.8 mL of diisopropyl ether cooled to 5° C., and a precipitate was collected by filtration. Slurry washing with the diisopropyl ether and filtration were repeated three times, and the precipitate was collected by filtration. The precipitate was dried under reduced pressure to afford 9 mg of Fmoc-L-Cys-NH$_2$.

ESIMS MNa+ 364.9

Example 13

Study on Increase in Solubility with Respect to Peptide Compounds

The solubility of a compound protected by the xanthene protective agent of the present invention was measured. FIG. 1 shows the results.

Peptide used as a model: H-Phe-Leu-NH$_2$

H-Phe-Leu-NH$_2$ and H-Phe-Leu-NH-(TIPS2-Xtn) were synthesized, and each compound was saturated in cyclopentyl methyl ether (CPME) at 25° C. to measure the solubility of each compound.

In regard to H-Phe-Leu-NH$_2$ not bound to a TIPS type protective agent, 0.5 mM of the peptide dissolved in CPME. Compared to that case, when H-Phe-Leu-NH$_2$ was bound to TIPS2-Xtn-NH$_2$, 586 mM of the peptide, which is about 1100 times or more the amount of the peptide in the former case, dissolved in CPME, indicating that the latter case improved in solubility. The results are shown in FIG. 1. From these results, it was found that derivatization with the xanthene protective agent leads to a significant improvement in solubility of the peptide. Herein, H-Phe-Leu-NH$_2$ and H-Phe-Leu-NH-(TIPS2-Xtn) have the following structures.

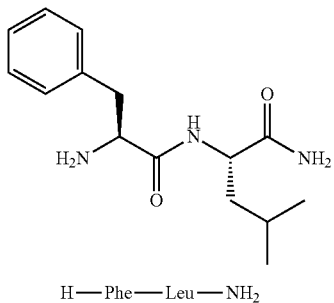

H—Phe—Leu—NH₂

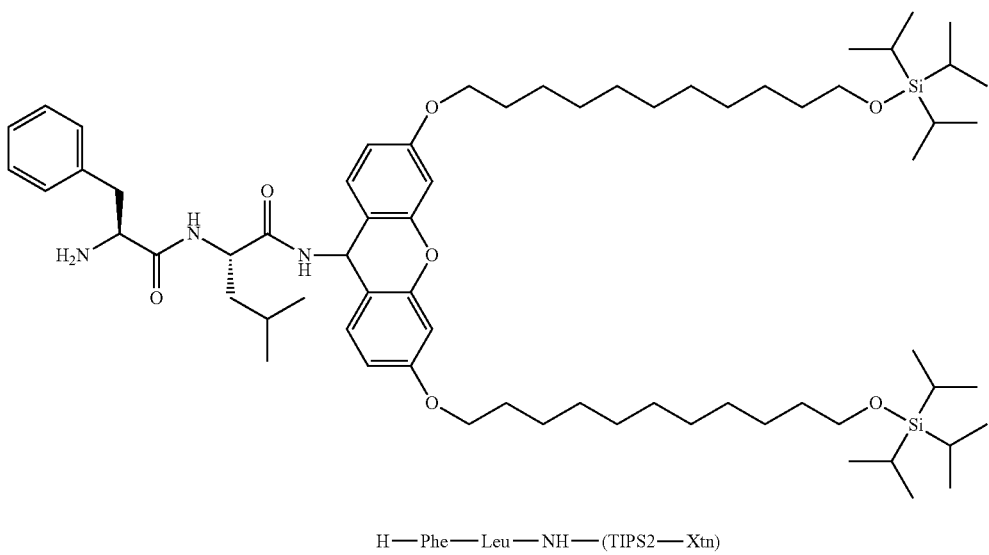

H—Phe—Leu—NH—(TIPS2—Xtn)

Example (13-a)

Synthesis of H-Phe-Leu-NH-(TIPS2-Xtn)

1.67 g (1.89 mmol) of TIPS2-Xtn-NH₂ was dissolved in 18.9 mL of CPME. To the resultant, added were 8.1 mL of DMF, 1.32 mL (7.55 mmol) of DIPEA, 1.00 g (2.83 mmol) of Fmoc-Leu-OH, 0.40 g (2.83 mmol) of ethyl cyano(hydroxyimino)acetate (Oxyma), and 1.21 g (2.83 mmol) of (1-cyano-2-ethoxy-2-oxoethylideneaminooxy)dimethyl-amino-morpholino-carbenium hexafluorophosphate (COMU), and the mixture was stirred at room temperature for 50 minutes. After checking the disappearance of TIPS2-Xtn-NH₂, 112 μL (1.13 mmol) of 2-(2-aminoethoxy)ethanol was added to the solution, and the solution was stirred at room temperature for 15 minutes. To the reaction solution, 4.04 g (22.6 mmol) of sodium 3-mercapto-1-propanesulfonate dissolved in 18.9 mL of DMSO was added, and 1.9 mL of DMSO and 2.12 mL (14.2 mmol) of DBU were added thereto. Then, the solution was stirred for 40 minutes. After checking the disappearance of Fmoc-Leu-NH-(TIPS2-Xtn), and after cooling the solution to 5° C., 3.72 mL (14.9 mmol) of 4 M CPME/HCl was dropped to the solution, and the solution was warmed up to room temperature. Then, 0.8 mL of CPME, 80 mL of 20% sodium chloride aqueous solution, and 68 mL of a 10% sodium carbonate aqueous solution were added to the solution, and the solution was separated and washed. To the resulting organic layer, 0.6 mL of DMSO, 0.6 mL of DMF, and 23 mL of a 50% dipotassium hydrogen phosphate aqueous solution were added, and the solution was separated and washed to afford a mixed solution containing H-Leu-NH-(TIPS2-Xtn). Herein, Fmoc-Leu-NH-(TIPS2-Xtn) and H-Phe-Leu-NH-(TIPS2-Xtn) have the following structures.

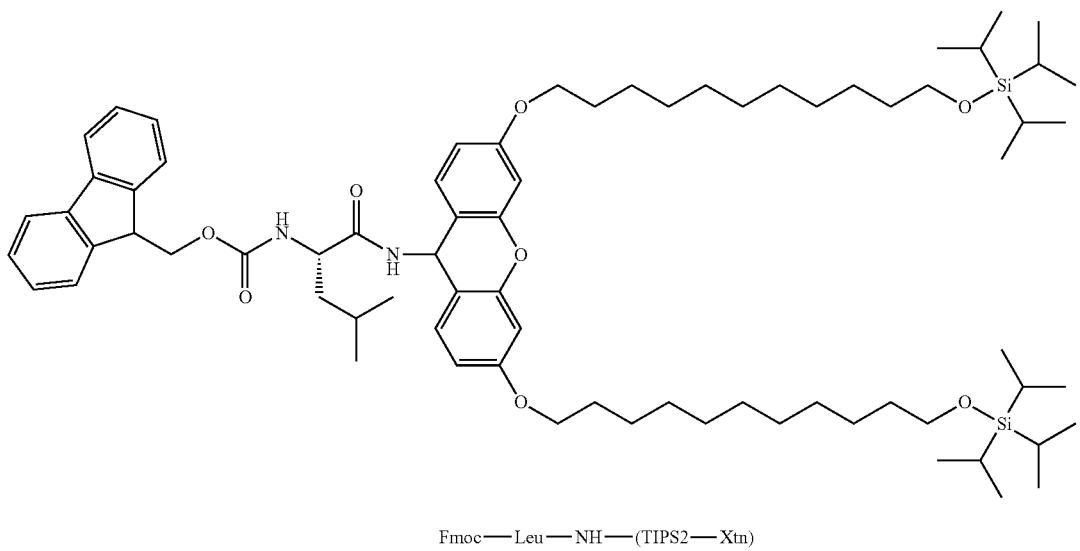

Fmoc—Leu—NH—(TIPS2—Xtn)

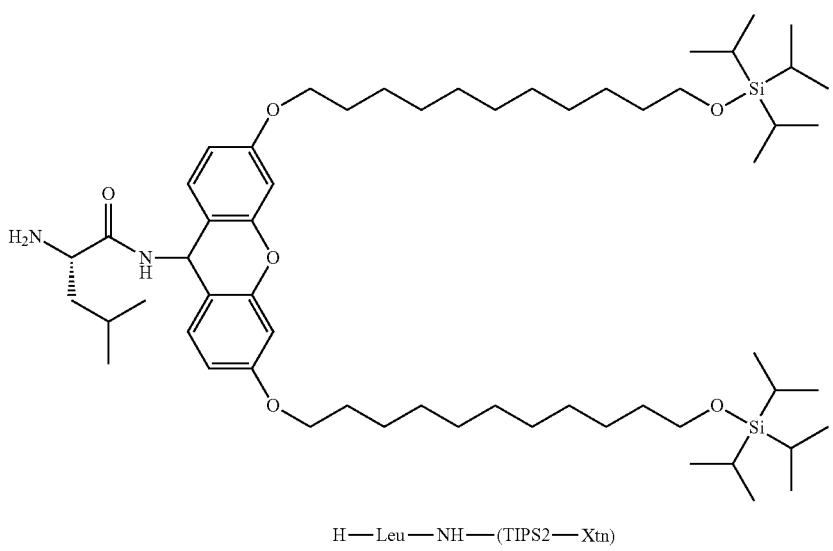

H—Leu—NH—(TIPS2—Xtn)

To the resulting mixed solution, added were 3.4 mL of CPME, 11.3 mL of DMF, 1.31 mL (7.55 mmol) of DIPEA, 1.10 g (2.83 mmol) of Fmoc-Phe-OH, 0.40 g (2.83 mmol) of Oxyma, and 1.21 g (2.83 mmol) of COMU, and the solution was stirred at room temperature for 50 minutes. After checking the disappearance of H-Leu-NH-(TIPS2-Xtn), 112 µL (1.13 mmol) of 2-(2-aminoethoxy)ethanol was added to the solution, and the solution was stirred at room temperature for 15 minutes. To the solution, 4.04 g (22.6 mmol) of sodium 3-mercapto-1-propanesulfonate dissolved in 18.9 mL of DMSO was added, and the solution was cooled to 5° C. Then, 1.9 mL of DMSO, and 2.12 mL (14.2 mmol) of DBU were added to the solution, and the solution was stirred for 35 minutes. After checking the disappearance of Fmoc-Phe-Leu-NH-(TIPS2-Xtn), 3.72 mL (14.9 mmol) of 4 M CPME/HCl was dropped to the solution, and the solution was warmed up to room temperature. Then, 0.9 mL of CPME, 88 mL of 20% sodium chloride aqueous solution, and 75 mL of a 10% sodium carbonate aqueous solution were added to the solution, and the solution was separated and washed. To the resulting organic layer, 0.8 mL of DMSO, 0.8 mL of DMF, and 31 mL of a 50% dipotassium hydrogen phosphate aqueous solution were added, and the solution was separated and washed. The solution was concentrated under reduced pressure, and a resulting residue was dissolved in 66 mL of heptane and separated and washed twice with 28 mL of acetonitrile. The heptane layer was concentrated under reduced pressure, and a resulting residue was dried under reduced pressure to yield afford 1.75 g of H-Phe-Leu-NH-(TIPS2-Xtn).

ESIMS MNa+ 1164.8

Herein, Fmoc-Phe-Leu-NH-(TIPS2-Xtn) has the following structure.

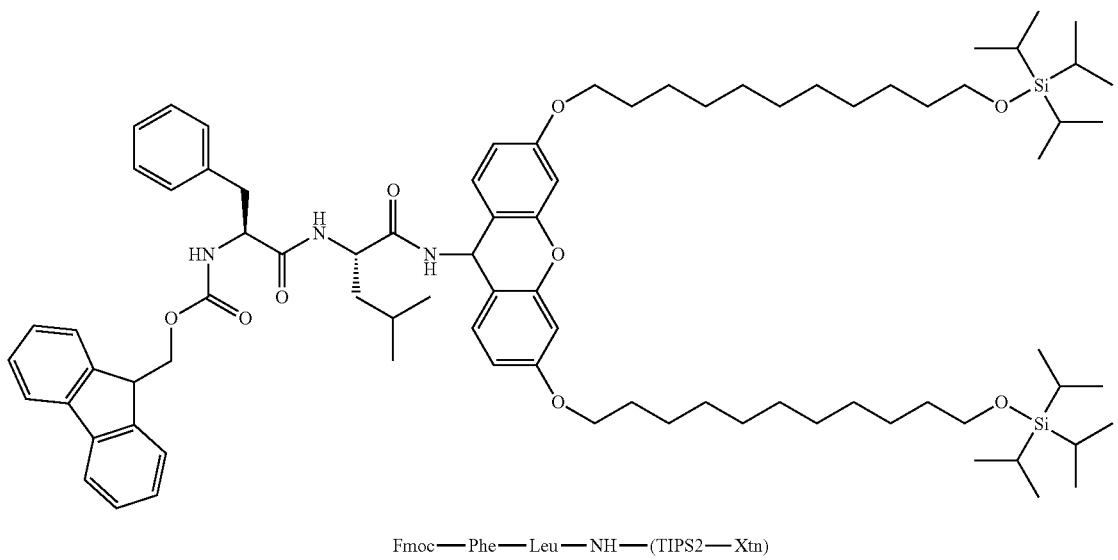

Fmoc—Phe—Leu—NH—(TIPS2—Xtn)

Example (13-b)

Synthesis of H-Phe-Leu-NH₂

209 mg (0.18 mmol) of H-Phe-Leu-NH-(TIPS2-Xtn) was dissolved in 3.23 mL of dichloromethane. To the solution, 0.37 mL (5.10 mmol) of trifluoroethanol, and 73 μL (0.96 mmol) of trifluoroacetic acid were added, and the solution was stirred at room temperature for 1 hour and 10 minutes. After checking the disappearance of H-Phe-Leu-NH-(TIPS2-Xtn), the solution was concentrated under reduced pressure, and a residue was dropped to 18.8 mL of diisopropyl ether cooled to 5° C. The residue was then centrifuged at 3000 rpm for 4 minutes at 5° C., and a supernatant was removed by decantation, whereby giving a precipitate. Slurry washing with the diisopropyl ether, centrifugation, and decantation were repeated three times to obtain a precipitate. The precipitate was dried under reduced pressure to afford 49 mg of H-Phe-Leu-NH₂.

ESIMS MH+ 278.0

From the above results, it was found that a compound including a functional group protected by the xanthene protective agent of the present invention has markedly enhanced solubility in an organic solvent.

The invention claimed is:

1. A xanthene compound of General Formula (1)

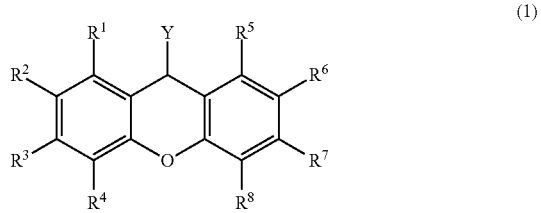

(1)

wherein:
Y is:
—OR$^{17}$, wherein R$^{17}$ is a hydrogen atom or an active ester-protecting group,
—NHR$^{18}$, wherein R$^{18}$ is a hydrogen atom, or a linear or branched C$_1$-C$_6$ alkyl group or aralkyl group,
an azide,
a halogen atom, or
a carbonyl group formed together with a methylene group;
at least one of R$^1$ to R$^8$ is represented by Formula (2), $$—O—R^9—X-A \quad (2)$$

and each of the remaining R$^1$ to R$^8$ independently is a hydrogen atom, a halogen atom, a C$_1$-C$_4$ alkyl group, or a C$_1$-C$_4$ alkoxy group,
wherein R$^9$ is a linear or branched C$_1$-C$_{16}$ alkylene group;
X is O or CONR$^{19}$, wherein R$^{19}$ is a hydrogen atom or a C$_1$-C$_4$ alkyl group; and
A is represented by Formula (3), (4), (5), (6), (7), (8), (9), (10), (11), (12), or (13)

(3)

(4)

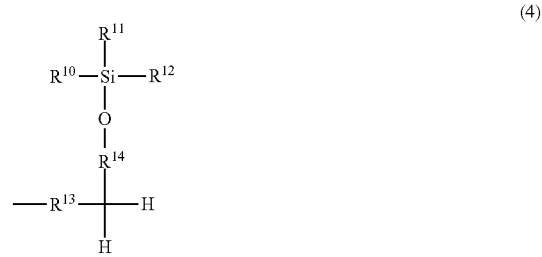

(5)

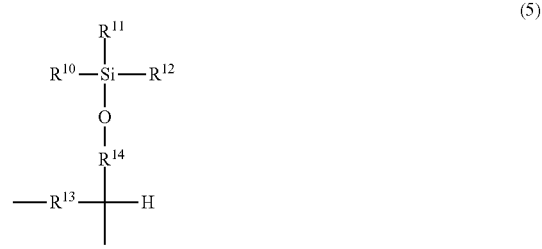

(6) 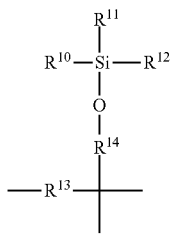

(7) 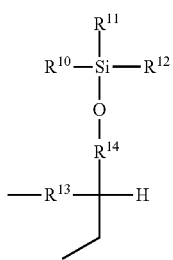

(8) 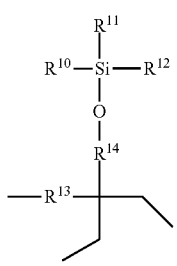

(9) 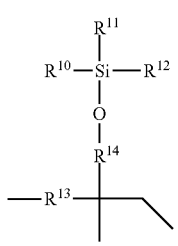

(10) 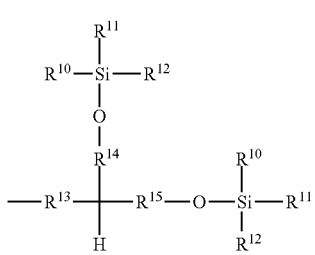

(11) 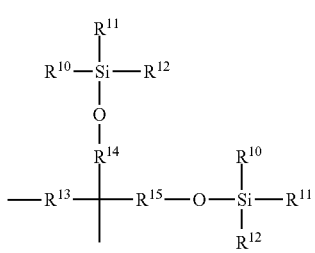

(12) 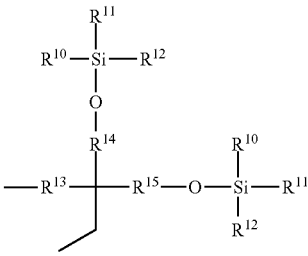

(13) 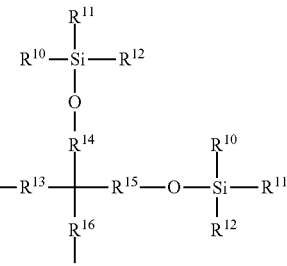

wherein $R^{10}$, $R^{11}$, and $R^{12}$ are each independently a linear or branched $C_1$-$C_6$ alkyl group or an aryl group optionally including a substituent;

$R^{13}$ is a single bond or a linear or branched $C_1$-$C_3$ alkylene group; and $R^{14}$, $R^{15}$, and $R^{16}$ are each independently a linear or branched $C_1$-$C_3$ alkylene group.

2. The xanthene compound according to claim 1, wherein Y is:
- —$OR^{17}$, wherein $R^{17}$ is a hydrogen atom or an active ester-protecting group,
- —$NHR^{18}$, wherein $R^{18}$ is a hydrogen atom, or a linear or branched $C_1$-$C_6$ alkyl group or aralkyl group,
- an azide, or
- a halogen atom.

3. The xanthene compound according to claim 1, wherein Y is:
- —$OR^{17}$, wherein $R^{17}$ is a hydrogen atom or an active ester-protecting group), or
- —$NHR^{18}$, wherein $R^{18}$ is a hydrogen atom, or a linear or branched $C_1$-$C_6$ alkyl group or aralkyl group.

4. The xanthene compound according to claim 1, wherein Y is:
- —$OR^{17}$, wherein $R^{17}$ is a hydrogen atom,
- —$NHR^{18}$, wherein $R^{18}$ is a hydrogen atom, or
- a carbonyl group formed together with a methylene group.

5. The xanthene compound according to claim 1, wherein Y is:
- —$OR^{17}$, wherein $R^{17}$ is a hydrogen atom, or
- —$NHR^{18}$, wherein $R^{18}$ is a hydrogen atom.

6. The xanthene compound according to claim 1, wherein at least one of $R^1$ to $R^8$ is a group represented by Formula (2), and each of the remaining $R^1$ to $R^8$ independently is a hydrogen atom, a $C_1$-$C_4$ alkyl group, or a $C_1$-$C_4$ alkoxy group.

7. The xanthene compound according to claim 1, wherein $R^9$ is a linear or branched $C_2$-$C_{16}$ alkylene group.

8. The xanthene compound according to claim 1, wherein $R^9$ is a linear or branched $C_6$-$C_{16}$ alkylene group.

9. The xanthene compound according to claim 1, wherein $R^{13}$ is a single bond or a methylene group, and $R^{14}$, $R^{15}$, and $R^{16}$ are each a methylene group.

10. A protective agent for protecting a carboxy group, a hydroxy group, a diol group, an amino group, an amide group, or a mercapto group, wherein the protective agent comprises the xanthene compound according to claim 1.

11. A method for producing a compound with a protective agent for protecting a carboxy group, a hydroxy group, a diol group, an amino group, an amide group, or a mercapto group, the method comprising reacting the carboxy group, hydroxy group, diol group, amino group, amide group, or mercapto group, with the protective agent, wherein the protective agent comprises the xanthene compound according to claim 1.

12. A method for producing a peptide with a protective agent for protecting a carboxy group, a hydroxy group, a diol group, an amino group, an amide group, or a mercapto group, the method comprising reacting the carboxy group, hydroxy group, diol group, amino group, amide group, or mercapto group, with the protective agent, wherein the protective agent comprises the xanthene compound according to claim 1.

* * * * *